US006923178B2

(12) United States Patent
Snow

(10) Patent No.: US 6,923,178 B2
(45) Date of Patent: Aug. 2, 2005

(54) MEDICAMENT CONTAINER WITH SAME SIDE AIRFLOW INLET AND OUTLET

(75) Inventor: John M. Snow, Raleigh, NC (US)

(73) Assignee: Innovative Devices, LLC., Raleigh, NC (US)

(*) Notice: Subject to any disclaimer, the term of this patent is extended or adjusted under 35 U.S.C. 154(b) by 89 days.

(21) Appl. No.: 10/099,282

(22) Filed: May 9, 2002

(65) Prior Publication Data

US 2002/0134382 A1 Sep. 26, 2002

Related U.S. Application Data

(62) Division of application No. 09/568,643, filed on May 10, 2000.

(51) Int. Cl.[7] ................................................ B65D 83/06

(52) U.S. Cl. ............... 128/203.15; 604/58; 128/203.12; 128/203.21; 128/203.23

(58) Field of Search ....................... 128/200.14–200.24, 128/203.12–204.14, 205.24, 207.14–207.18; 604/57–61

(56) References Cited

U.S. PATENT DOCUMENTS 3,906,950 A 9/1975 Cocozza
3,991,761 A * 11/1976 Cocozza ................ 128/203.15
4,338,931 A 7/1982 Cavazza
4,423,724 A 1/1984 Young
4,627,432 A 12/1986 Newell et al.
4,778,054 A 10/1988 Newell et al.
4,805,811 A 2/1989 Wetterlin
4,811,731 A 3/1989 Newell et al.
4,995,385 A * 2/1991 Valentini et al. ....... 128/203.21
5,033,463 A 7/1991 Cocozza
5,035,237 A 7/1991 Newell et al.
5,161,524 A 11/1992 Evans
5,201,308 A 4/1993 Newhouse
5,320,714 A 6/1994 Brendel
5,327,883 A 7/1994 Williams et al.
5,337,740 A 8/1994 Armstrong et al.
5,347,999 A 9/1994 Poss et al.
5,388,572 A 2/1995 Mulhauser et al.
5,408,994 A 4/1995 Wass et al.
5,415,162 A 5/1995 Casper et al.
5,437,271 A 8/1995 Hodson et al.
5,447,151 A 9/1995 Bruna et al.
5,482,032 A 1/1996 Smith et al.
5,483,954 A 1/1996 Mecikalski
5,529,059 A 6/1996 Armstrong et al.
5,533,502 A * 7/1996 Piper ..................... 128/203.21
5,577,497 A 11/1996 Mecikalski et al.

(Continued)

FOREIGN PATENT DOCUMENTS

| | | | |
|---|---|---|---|
| EP | 0211595 | A2 | 2/1987 |
| EP | 0467172 | A1 | 1/1992 |
| GB | 2165159 | A | 4/1986 |
| GB | 2264 | | 8/1993 |
| GB | 2340758 | | 1/2000 |
| WO | WO90/13328 | | 11/1990 |

*Primary Examiner*—Glenn K. Dawson
(74) *Attorney, Agent, or Firm*—Bateman IP Law Group

(57) ABSTRACT

A medicament container configured to improve entrainment of the medicament in the air and to improve deposition of the medicament in the lungs includes an upper layer and a bottom layer with medicament disposed therebetween. The upper layer is punctured to provide first and second openings to allow airflow to enter and exit through the upper layer of the medicament container. In a preferred embodiment, the medicament container has a projection which forms an elbow-shaped medicament containment/flow channel between the upper layer and the lower layer. The medicament container is preferably used in a housing which selectively controls airflow through the medicament container and the housing to improve deep lung deposition of the medicament.

36 Claims, 20 Drawing Sheets

U.S. PATENT DOCUMENTS

| | | | |
|---|---|---|---|
| 5,622,166 A | | 4/1997 | Eisele et al. |
| 5,647,349 A | * | 7/1997 | Ohki et al. ............ 128/203.15 |
| 5,657,749 A | | 8/1997 | Cox et al. |
| 5,660,169 A | | 8/1997 | Kaellstrand et al. |
| 5,692,496 A | | 12/1997 | Casper et al. |
| 5,715,810 A | | 2/1998 | Armstrong et al. |
| 5,740,794 A | * | 4/1998 | Smith et al. ............ 128/203.15 |
| 5,752,505 A | * | 5/1998 | Ohki et al. ............ 128/203.15 |
| 5,794,613 A | | 8/1998 | Piskorski |
| 5,810,004 A | | 9/1998 | Ohki et al. |
| 5,823,183 A | | 10/1998 | Casper et al. |
| 5,875,776 A | | 3/1999 | Vaghefi |
| 5,896,855 A | | 4/1999 | Hobbs et al. |
| 5,921,237 A | | 7/1999 | Eisele et al. |
| 5,988,163 A | | 11/1999 | Casper et al. |

\* cited by examiner

MEDICAMENT CONTAINER WITH SAME SIDE AIRFLOW INLET AND OUTLET

RELATED APPLICATION

The present application is a division of U.S. patent application Ser. No. 09/568,643, filed May 10, 2000 now pending.

BACKGROUND OF THE INVENTION

1. Field of the Invention

The present invention relates to an improved medicament inhalator. More particularly, the present invention relates to an improved dry powder medicament container usable by asthmatics and the like to facilitate proper deposition of the medicament in the lungs. The dry powder medicament inhalator uses a novel piercing mechanism and flow configuration to access the medicament and improve supply of the medicament to the lungs of the user.

2. State of the Art

The widespread existence of asthma and other respiratory disorders has lead to the development of numerous medications which can be used to open restricted breathing passages or otherwise enable the user to breathe more easily. While some asthmatics suffer from only occasional or minor attacks, for many breathing is a constant struggle made possible only by frequent use of appropriate medication. These medications may be in either dry or liquid form, depending on the type of medication and the particular problems faced by the user.

There are essentially two types of inhalation devices currently available in the marketplace for the administration of a medicament to the lungs. The predominant inhalation device is a pressurized, metered dose inhaler (MDI) which contains medicament suspended in a pharmaceutically inert liquid propellant, e.g., chlorofluorocarbons (CFCs) or hydrofluorocarbons (HFCs). MDIs are well known in the art and are commonly used.

These propellant-based inhalation devices have the advantage of consistently delivering a predetermined dose of medication from the aerosol canister. However, the drug particles are typically propelled at high velocity from the inhalation device. A significant quantity of the medication impacts tissue in the mouth or throat of the patient, becoming unavailable for deposition in the lungs. Furthermore, growing concern over the link between depletion of atmospheric ozone and chlorofluorocarbon propellants has focused attention on the development of alternative means of delivering medication to the lungs, including the development of dry powder inhalation systems.

Dry powder inhalers represent the second major type of inhalation devices. Dry powder inhaler devices known to the applicants and existing in the marketplace utilize the patient's inhaled breath as a vehicle to transport the dry powder drug to the lungs. Because the medicament is carried into the lungs during inhalation, less medicament is lost to the lining of the mouth and throat. Additionally, using the patient's inhalation increases the amount of medicament which reaches deep within the lungs where medicament is often needed most.

Presently there are four principal methods in use to provide fine particulate powder to the lungs without the use of chlorofluorocarbons or other propellants. One common method relies on the use of a hard gelatin capsule which contains a pre-measured dose of therapeutically active material and an inhalator device for use with the capsule. The capsule is placed in the inhalator device which serves to open or perforate the capsule, exposing the dose of medicament. The medicament is removed from the capsule by the vacuum action created when the patient inhales through the mouthpiece of the device, and is entrained in the inspired air stream for transport to the patient's lungs. The empty capsule is removed from the inhalation device after each use.

Inhalators using this type of capsule technology are described in U.S. Pat. No. 3,807,400 (Cocozza); U.S. Pat. No. 3,906,950 (Cocozza); U.S. Pat. No. 3,991,761 (Cocozza) and U.S. Pat. No. 4,013,075 (Cocozza). The intent in each of these devices is to remove all of the powdered medicament from the interior of the capsule. However, it has been found that the air stream generated by the patient is typically insufficient to accomplish complete removal of medicament from the capsule. This can be especially true for a patient having reduced inhalation ability due to an asthma attack.

Additionally, gelatin capsules are affected by relative humidity during storage and may become hydrated in moist environments. Hydration results in poor opening of the capsule and agglomeration of the powder contents. In dry climates, the capsules can become dehydrated, resulting in brittle fracture of the capsule, potentially making fine gelatin fragments available for inhalation or compromising dosing due to electrostatic attraction of medicament to the capsule surfaces.

A second method for delivery of dry powder medicaments relies on providing a package containing multiple doses of medicament, each contained in a sealed blister. The package is used in conjunction with a specially designed inhalation device which provides a means of attachment for the package and perforation of an individual blister by the patient prior to the inhalation of its contents. Delivery systems of this type are described in EPO Patent Application Publication No. 0 211 595 A2 (Newell et al.); EPO Patent Application Publication No. 0 455 463 A1 (Velasquez et al.); and EPO Patent Application Publication No. 0 467 172 A1 (Cocozza et al.). As the patient inhales, a portion of the inhaled air stream flows continuously through the perforated blister entraining the medicament and providing for inclusion of the medicament in the inspired breath. Delivery of medicament to the patient's inspired air stream begins as sufficient flow develops through the blister for removal of the medicament. No means is provided by which the point or rate of delivery of medicament to the patient is controlled.

A third method for delivery of dry powder medicaments involves the use of a device equipped with a drug reservoir containing sufficient medicament for a much larger number of doses. The Draco TURBUHALER® is an example of this type of device and is described in detail in U.S. Pat. No. 4,688,218 (Virtanen); U.S. Pat. No. 4,667,668 (Wetterlin); and U.S. Pat. No. 4,805,811 (Wetterlin). The device provides a means for withdrawing a dose of medicament from the reservoir and presenting the withdrawn dose for inhalation by the patient. As the patient inhales through the mouthpiece of the device, the medicament contained in perforations in a dosing plate is entrained in the inspired air and flows through a conduit or conduits. The conduits serve as a vortex creating a means for breaking up powder agglomerates before the medicament becomes available to the patient. Moisture ingress in the reservoir results in agglomeration of the powder contents, compromising dosing due to retention of powder in the perforations in the dosing plate and potentially inadequate breakup of particulates in the inspired air stream.

A fourth method for delivery of dry powder medicaments involves the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device. Devices of this general type are described in PCT WO 93/12831 (Zirerenberg et al.); German Patent No. DE 4133274 A1 (Kühnel et al.); German Patent No. DE 4020571 A1 (Hochrainer et al.); and U.S. Pat. No. 5,388,572 (Mulhauser et al.). The incorporation of a piston system, in each case, adds to the complexity of the inhalation device, both in terms of use by the patient and device manufacturability.

A recent improvement in dry powder inhalators is contained in U.S. Pat. No. 5,988,163 for a Dry Powder Medicament Inhalator Having an Inhalation-Activated Flow Diverting Means for Triggering Delivery of Medicament. The inhalator disclosed therein utilizes a configuration which increases deep lung penetration of the medicament and reduces agglomerations.

While considerable progress in dry power inhalators has been made over the last decade, there is still considerable room for improvement. For example, in many configurations which use a blister pack, the medicament is accessed by advancing a lancet through the blister pack so that airflow will enter the top of the blister pack and exit through the bottom with the medicament entrained therein. Such configurations, however, have several distinct disadvantages.

First, as the blister pack is pierced by the lancet, it is not uncommon for the foil to be pushed out of the lancet's way in such a manner that the foil encapsulates or partially encapsulates a portion of the medicament. The deformed portions of the blister pack often prevent a portion of the medicament from being entrained in the airflow and thus reduce the amount of medicament going to the patient.

Second, advancing the lancet through the blister pack leaves an opening through which the medicament may fall. Usually, this does not present a problem, as the medicament will fall into a portion of the inspiratory flow channel and will be delivered properly once the user inhales. If, however, the lancet is accidentally actuated or the user forgets that the lancet has already been actuated, the blister pack may be advanced to position the next blister below the lancet while medicament remains in the inspiratory flow channel. Once the lancet has been actuated again and the user inhales, the user receives a double dose of the medicament. (If a child were to play with the inhalator and repeatedly advance and lance the blister pack, it is conceivable that a very large dose could be left within the inhalation channel of the inhalator.) With some asthma medications, accidentally supplying a double dose is undesirable and potentially dangerous to the patient.

Thus, there is a need for an improved medicament container and for a method and mechanism for actuating the same, wherein the container and inhalator controls medicament flow to ensure that the medicament is properly deposited in the lungs. Such a device preferably should be configured to release medicament into the inspiratory air stream and avoid leaving a therapeutically significant amount of medicament in the blister pack. Such a configuration should also inhibit simultaneous double or multiple dosing. Such a configuration should also be relatively inexpensive and convenient to use.

OBJECTS OF THE INVENTION

It is an object of the present invention to provide a medicament container for the administration of dry powder medicament which improves medicament flow to maximize delivery of the medicament to the lungs. The medicament may be pure drug particles, or may be drug particles attached to a carrier particle, e.g. lactose.

It is another object of the present invention to provide such a medicament container which is easy to use and which has either multiple dosing capabilities, and/or the ability to be conveniently reloaded.

It is another object of the present invention to provide such a medicament container which retains the medicament within the container until it is entrained in inspiratory air.

It is yet another object of the present invention to provide a method for removing medicament from a container which improves entrainment of the medicament in the inspiratory air. Yet another object of the present invention is to provide such a medicament container which is functionally simple and relatively inexpensive.

It is still yet another object of the present invention to provide al inhalator which interacts with the medicament container to improve entrainment of the medicament in the inspiratory air.

The above and other objects of the invention are realized in specific illustrated embodiments of a medicament container which is punctured to provide same side air inflow and outflow to improve entrainment of the medicament in the air and to improve deposition of the medicament in the lungs.

In accordance with one aspect of the present invention, the medicament container is provided with an upper surface and a lower surface. The upper surface is generally planar and formed from foil, plastic or similar material which may be easily punctured and deformed by a lancing mechanism. The opposing lower surface of the medicament container is concave to form a blister containing medicament. Preferably, the lower surface is formed of a more rigid material, such as Aclar or polycarbonate, which resists punctures, collapsing or other damage.

In accordance with the method of the present invention, holes are formed by a lancet at opposing lateral sides along the upper surface. Inspiratory air is channeled in through one hole in the upper surface, into contact with the medicament, and out through the opposing hole. In accordance with the principles of the present invention, it has been found that such a flow configuration improves entrainment of the medicament and delivery of the medicament to the lungs of the user. Such a configuration also helps prevent loss of medicament if the inhalator is tipped or jarred during use.

In accordance with another aspect of the present invention, a flow diverter is disposed within the blister formed by the upper layer and the lower layer. The flow diverter helps to channel inspiratory air in a desired flow pattern. Preferably, the flow diverter is formed from a relatively rigid material, such as polycarbonate and is disposed adjacent to the upper layer. The flow diverter extends downwardly in a concave manner which preferably runs generally parallel to the concave curvature in the lower layer to form a generally elbow-shaped channel for the medicament with the medicament being concentrated at the bend in the elbow.

In use, the lancet forms holes at both ends of the elbow-shaped channel. When the user inhales, inspiratory air enters the blister at one end of the channel, follows the elbow-shaped channel and entrains the medicament and exits through the opposing end of the elbow shaped channel. In accordance with the present invention, it has been found that such a configuration improves medicament entrainment and decreases the amount of therapeutic material retained in the blister.

In accordance with another aspect of the invention, the medicament container is formed of at least an upper layer, a lower layer and a carrying tray. The lower layer of the medicament container is formed from a semi-rigid material such as polyvinyl chloride (PVC), polyvinyl dichloride (PvdC), or fluoronated and/or chloronated homopolymers/copolymers (Aclar), while the carrying tray is formed by a more rigid material such as polycarbonate. The lower layer is formed with a structure that mates with the carrying tray. Thus, an initial medicament container can be formed and then nested in the carrying tray for added durability.

In accordance with another aspect of the present invention, actuation of the lancet causes the lancet to engage the upper surface of the medicament container and to puncture the foil to form inspiratory air inlet and outlet openings. As the lancet punctures the foil, etc., the foil is pressed against an upper surface of the lower layer, to thereby fold the foil, etc., out of the flow path so that it will not disturb the flow of medicament.

In accordance with yet another aspect of the present invention, a sealing member is disposed adjacent to the medicament container. The sealing member helps regulate airflow into and out of the container so that inspiratory airflow follows the desired path. When used in conjunction with the lancet which presses the foil upper surface out of the way, the sealing member is able to move along the upper surface if needed without encountering pieces of foil extending above the upper surface.

In accordance with yet another aspect of the present invention, a portion of the lancet defines a portion of the inspiratory air flow channel. The lancet helps to direct inspiratory air along the desired path to provide the desired medicament flow pattern.

In one embodiment, the lancet has two prongs, the lower end of each being beveled. To puncture the upper surface of the medicament container, the lancet is advanced until the beveled portions of each prong has punctured the container. The lancet is then allowed to withdraw so that the beveled ends form part of the inspiratory inflow air channel and/or the inspiratory outflow air channel.

In accordance with another aspect of the invention, each of the prongs of the lancet may be partially hollow and configured to allow airflow therethrough while providing the desired resistance to flow. Airflow through the prongs is prevented until the prongs have punctured the upper surface of the medicament container. Once the lower end of each prong is in the medicament container, inspiratory airflow is enabled and medicament is entrained therein.

In accordance with still yet another aspect of the present invention, the formation of inflow and outflow holes in the upper surface of the medicament container facilitates puncturing of the medicament container with less effort due to the lancet only having to puncture the foil top layer of the blister.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1A:
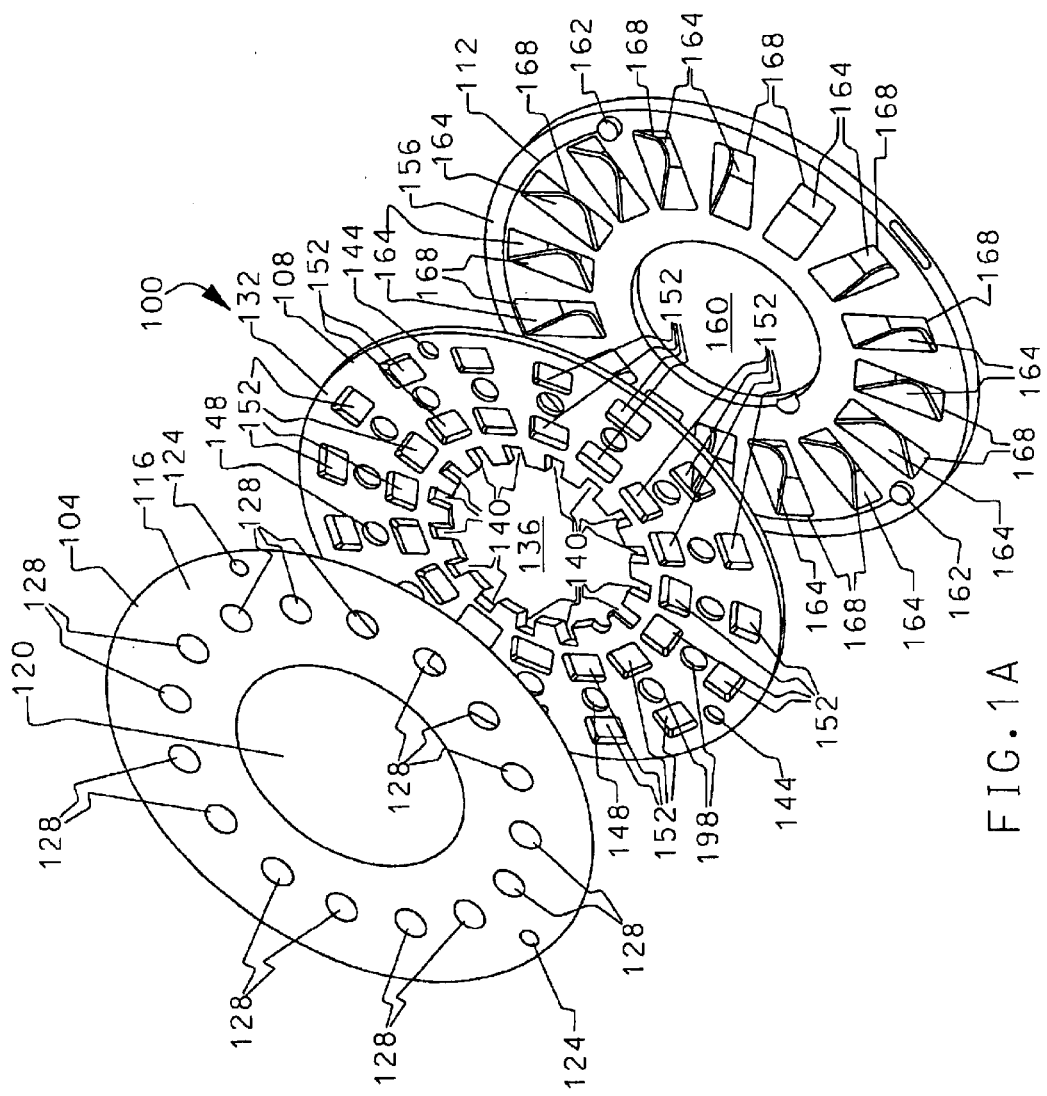
FIG. 1A a shows an top, exploded view of a medicament container made in accordance with the principles of the present invention and including an upper layer, a middle layer and a bottom layer.

Referring to FIG. 1A, there is shown a top, exploded view of a medicament container, generally indicated at 100, made in accordance with the principles of the present invention. The medicament container 100 includes an upper layer 104, a middle layer 108 and a bottom layer 112. In one preferred application of the principles of the present invention, the three layers 104, 108 and 112 are joined together to form a single container which provides improved control over storage and dispensing of medicament.

The upper layer 104 of the medicament container 100 is formed by a generally planar piece of material which may be readily punctured. In a presently preferred embodiment, the upper layer is formed by a piece of foil forming a disk 116. The use of foil for blister packs is well known to those skilled in the art and several types of foil are readily available. Other easily puncturable materials, such as plastic or paper could also be used.

The disk 116 forming the upper layer 104 has a central opening 120 formed therein. As will be explained in additional detail below, the opening is provided to facilitate support and rotation of the medicament container 100 during its use in a medicament dispensing housing, such as that discussed below with respect to FIG. 5A through 6C.

Disposed in the disk 116 are two openings 124 disposed opposite one another. The two openings receive a mating structure (discussed below) from bottom layer 112 to help hold the medicament container together and to help ensure proper alignment.

Also disposed in upper surface 104 are a plurality of openings 128 disposed in a generally circular pattern. The openings align with portions of the middle layer 108 and are used as an indexing and positioning means in conjunction with one embodiment of a medicament dispensing housing.

The middle layer 108 is also formed by a disk 132 which defines an opening 136. As shown in FIG. 1A, the inner wall 132a of the disk 132 which defines the opening 136 is provided with a plurality of notches 140. The notches 140 are configured to engage a rotation mechanism of an inhalator housing (not shown) so that the medicament container 100 can be rotated after each use to align medicament with a inspiratory flow channel (not shown).

The disk 132 forming the middle layer has a pair of openings 144 which are disposed opposite one another and in alignment with the openings 124 in the disk 116 of the upper layer 104. As with the openings 124, the openings 144 receive a mating structure 162 on the lower layer 112 to help align the middle layer 108 and to help retain the middle layer in place.

Disposed in the disk 132 is a plurality of openings 148 which are disposed in a generally circular arrangement. The openings 148 are configured to be in alignment with the openings 128 in the disk 116 of the upper layer 104. The openings are used to align the medicament container 100 with an indexing and positioning means of one embodiment of a medicament dispensing housing (not shown). While the openings 128 and 148 are preferable, those skilled in the art will appreciate that they can be omitted without significantly interfering with the operation of the medicament container 100.

Also disposed in the disk 132 defining the middle layer 108 are a plurality of openings 152 which are disposed in concentric circles. The openings 152 are generally square or rectangular and extend through the, disk 132 at a transverse angle. As will be discussed in additional detail below, the openings 152 are configured to receive portions of a lancet which punctures the upper layer 104 during use. The transverse angle of the openings 152 helps to channel airflow into and out of the medicament container 100 to improve entrainment of the medicament contained therein.

The portion of the disk 132 between the concentric circles of openings 152 supports the foil or other material of the upper layer 104 so that the opening formed by a lancet puncturing the upper layer is localized. A detailed discussion of the lancet mechanism is provided below with respect to FIGS. 3A and 3B.

In use, the disk 116 defining the upper layer 104 and the disk 132 defining the middle layer 108 are attached to a disk 156 which defines the lower layer 112. As will be explained in detail with respect to FIGS. 1D and 1E, the disk 156 which forms the lower layer in FIGS. 1A through 1C also forms a carrying tray. This is due to the fact that the disk 156 is preferably made out of a substantially rigid material, such as polycarbonate, to protect the medicament contained within the medicament container 100.

As with the upper layer 104 and the middle layer 108, the disk 156 of the lower layer 112 defines an opening 160. The opening 160 is preferably slightly larger than the opening 136 in the middle layer 108 so that it will not interfere with an engagement between a rotation actuation mechanism of an inhalator and the notches 140.

Extending upwardly from the disk 156 are a pair of mating structures 162. The mating structures 162 nest in the openings 124 of the upper layer 104 and the openings 144 of the middle layer 108 to help align the upper layer and middle layer with the bottom layer 112. The mating structures 162 can also be used to help retain the upper layer 104 and the middle layer 108.

The disk 156 which defines the lower layer 112 has a plurality of concave receptacles 164 formed therein. As shown in FIG. 1A, the receptacles 164 preferably have a generally rectangular opening 168 adjacent the top of the bottom layer 112. From the rectangular opening 168, the receptacles 164 extend downwardly and inwardly so that the receptacles have a generally triangular cross-section. The generally triangular cross-section of the receptacles 164 causes the medicament to collect in the bottom of the receptacle where it is less likely to interfere with opening of the receptacle by the lancet mechanism.

With conventional medicament containers referred to as blister packs, it is common for both the top layer and the bottom layer to be formed of foil so that a lancet can penetrate both layers. Penetrating through both layers forms an upper air inflow opening and a lower opening for the medicament entrained in the air to exit the blister pack. The disadvantages of such configurations are discussed above in the background section.

In the present invention, it is preferred that both the air inflow and outflow openings are formed in the upper layer 104 of the medicament container 100. Because it is not necessary to puncture the lower layer 112, the lower layer can be formed of materials which are much more durable than foil, paper, etc. It is preferable that the disk 156 of the lower layer 112 (and the disk 132 defining the middle layer 108) be made of plastic which is compatible with the medicament being used. Thus, for example, the lower layer 112 may be made of polycarbonate, polypropylene, polyurethane or some other easily moldable plastic. The lower layer 112 may also be relatively rigid as it will not be punctured by the lancet mechanism.

The use of a relatively rigid lower layer 112 has several distinct advantages. First, the rigidity helps to protect the medicament container 100 from being damaged during shipping or improper handling. Second, having the receptacles formed with a rigid bottom helps prevent medicament contained therein from being pressed upwardly into contact with the upper layer of the container.

In conventional blister packs, applying pressure to the bottom of the blister could cause the medicament to be compressed between the upper and lower layers. As the lancet penetrates through the blister, the punctured pieces of foil can engage the medicament and significantly interfere with entrainment of the medicament in the airflow passing through the blister. The medicament can also be compressed, increasing the risk of agglomeration of the medicament particles.

The substantially rigid triangular receptacles 164 of the lower layer 112, in contrast, receive and maintain the medicament away from the upper layer 104. As the foil, paper, etc., of the upper layer 104 is pierced, the medicament will generally be sufficiently far from the upper layer that the foil, etc., will have very little effect on airflow and medicament entrainment.

Figure 1B:
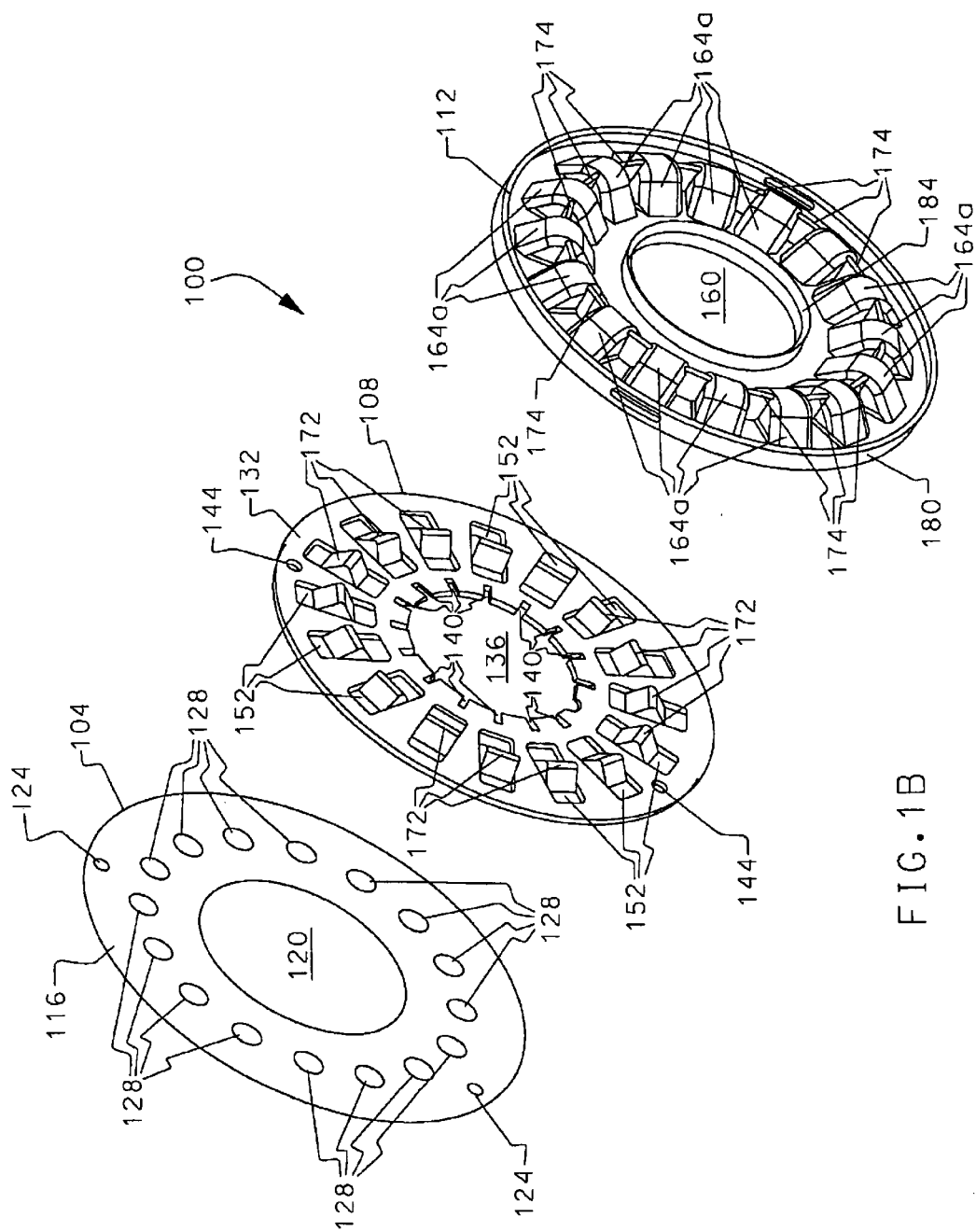
FIG. 1B shows a bottom, exploded view of the upper layer, middle layer and bottom layer of the medicament container of FIG. 1A.

Turning now to FIG. 1B, there is shown a bottom, exploded view of the medicament container 100 shown in FIG. 1A, including the upper layer 104, the middle layer 108 and the lower layer 112.

The view of the upper layer 104 differs little from that shown in FIG. 1A except that it is the underside of the same structure. Thus, the upper layer is numbered in accordance with numbering used in FIG. 1A.

The bottom view of the middle layer 108., in contrast, is substantially different than that shown in FIG. 1A. While the bottom view shows the disk 132 defining the hole 136, the openings 144 for receiving the mating structure 162, and the openings 152 for receiving the lancet (not shown), it also includes a plurality of projections 172.

The projections 172 are positioned between the outer and inner concentric circles defined by the openings 152. The projections 172 preferably have a triangular cross-section so that the projections will extend downwardly into the receptacles 164 when the middle layer 108 is attached to the lower layer 112. The projections 172, however, are preferably smaller and less deep than the receptacles 164. As will be explained in additional detail below, the projection 172 serves as a flow diverting means to improve medicament entrainment in the inspiratory air.

FIG. 1B also shows the bottom of the bottom layer 112, including the downwardly extending walls 164a which form the receptacles 164. To provide enhanced rigidity and resistance to damage of the receptacles, support walls 174 can extend between the walls 164a defining the receptacles. To add further support, the bottom layer 112 can have an outer annular collar 180 disposed about its circumference, and an inner annular collar 184 which circumscribes the opening 160.

With such support structures, the bottom layer 112 can be formed from a thin piece of rigid or semi-rigid plastic which is both very light weight and resistant to damage.

Figure 1C:
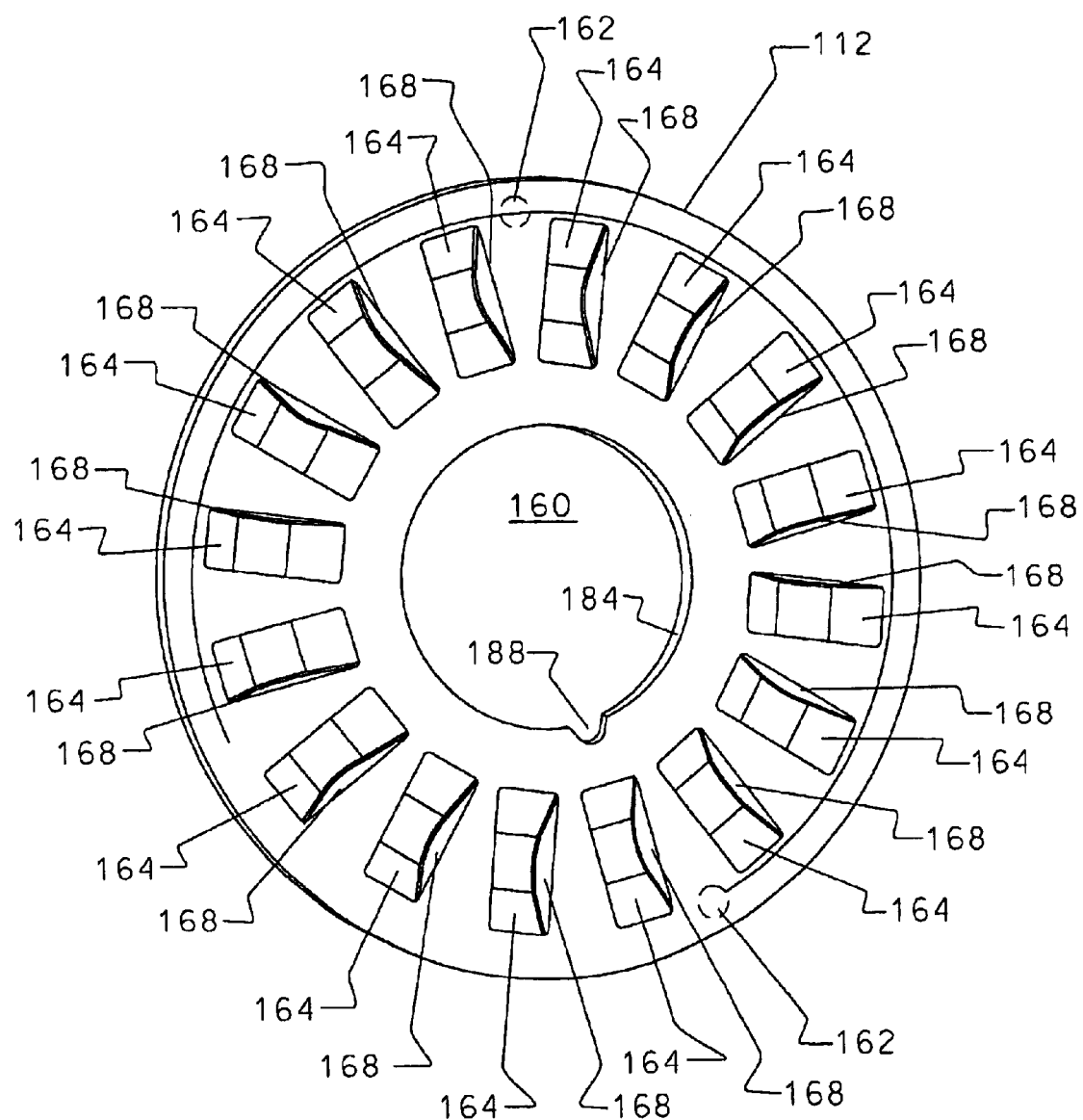
FIG. 1C shows a top view of the bottom layer shown in FIGS. 1A and 1B.

In FIG. 1C, there is shown a top view of the bottom layer 112 and the receptacles 164 which extend downwardly and inwardly from the openings 168 so as to provide a medicament holding compartment with a generally triangular cross-section. While the mating structures 162 are used to secure and align the middle and upper layers, such structures can also be used to help orient the medicament container 100 within the inhaler. Likewise, a groove 188 can be formed in the annular wall 184 circumscribing the opening 160 to provide orientation of the medicament container.

The medicament container preferably includes the upper layer 104, the middle layer 108, and the bottom layer 112. While the medicament container 100 could omit the middle layer 108 and still function in a manner superior to the prior art, the middle layer and the structures formed therein improve medicament entrainment and delivery to the patient.

Figure 1D:
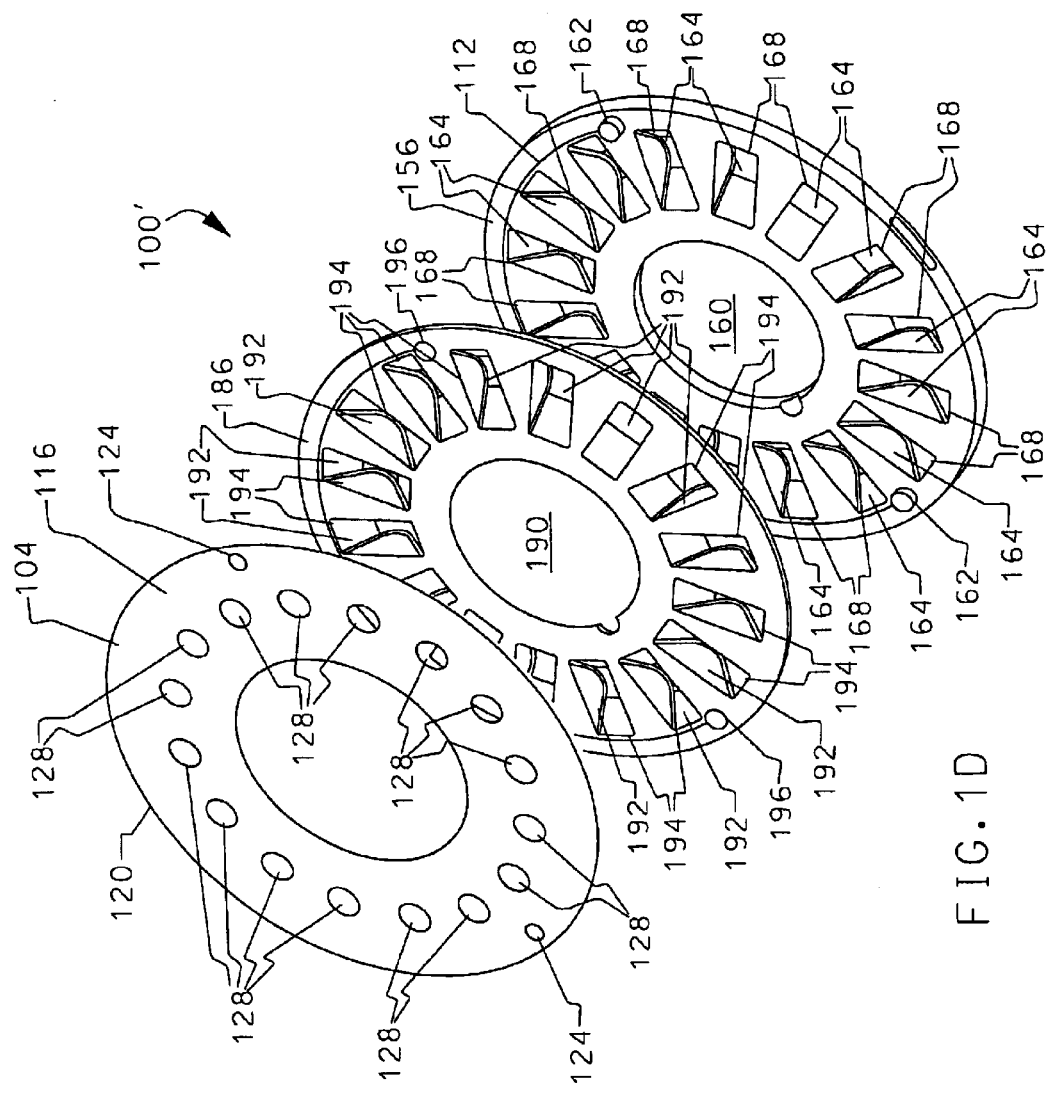
FIG. 1D shows an exploded view of an alternate embodiment of a medicament container made in accordance with the principles of the present invention.

Turning now to FIG. 1D, there is shown an exploded view of an alternate embodiment of a medicament container, generally indicated at 100' and made in accordance with the principles of the present invention. The medicament container 100' includes an upper layer which is preferentially configured the same as upper layer 104 in FIGS. 1A through 1C and is therefor numbered accordingly.

Normally attached to the upper layer 104 is a medicament carrying tray 186. The medicament carrying tray 186 is preferably formed of a semi-rigid material, such as polyvinyl chloride (PVC), polyvinyl dichloride (PvdC), or fluoronated and/or chloronated homopolymers/copolymers (Aclar).

The medicament carrying tray 186 is formed from a disk 188 with a central opening 190. The medicament carrying tray layer 186 has a plurality of concave receptacles 192 disposed concentrically around the opening for receiving medicament so that the powdered medicament is held between the upper layer 104 and the medicament carrying tray 186.

The receptacles 192 preferably have a generally triangular cross-section, with a rounded bottom, and generally rectangular openings 194 adjacent the top of the medicament carrying tray 186, and are otherwise similar to the receptacles 164 discussed in FIGS. 1A through 1C. The medicament carrying tray 186 may also include a pair of holes 196 for receiving mating structures of a carrying tray.

Disposed below the medicament carrying tray 186 is a lower layer which, as shown in FIG. 1D, is formed by the disk 156 discussed in FIGS. 1A through 1C. The receptacles 164 in the disk 156 are preferably sized to nestingly receive the receptacles 192 of the medicament carrying tray 186 so that the upper layer 104 and the medicament carrying tray can be securely held in the lower layer 112.

By providing the medicament container with a semi-rigid carrying tray 186 which then nests in a rigid lower layer 112, one can achieve all of the benefits identified above with having a rigid lower layer, while facilitating manufacture of the medicament container 100'.

Those skilled in the art will appreciate that while the upper layer 104 is normally attached to the medicament carrying tray 186, the upper layer and the medicament carrying tray need not be fixedly attached to the lower layer. Thus, for example, the upper layer and the medicament carrying tray could be removably disposed in a rigid lower layer 112 which could be permanently mounted in the housing of a medicament dispenser. In such a configuration, the user would only need to replace the combination of the upper layer 104 and the medicament carrying tray 186 each time the medicament contained in the medicament carrying tray was exhausted.

Figure 1E:
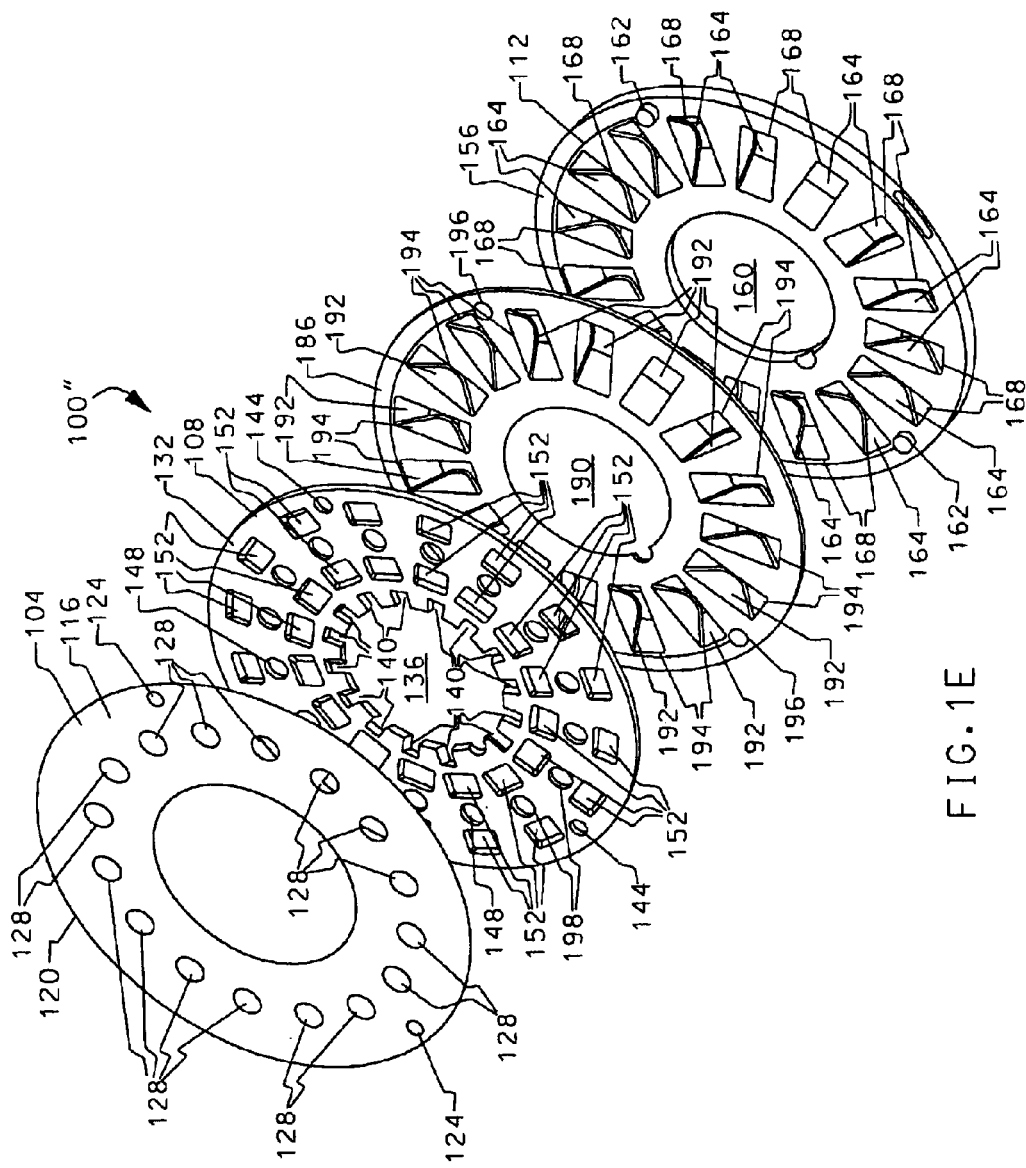
FIG. 1E shows an exploded view of yet another alternate embodiment of a medicament container made in accordance with the principles of the present invention.

Turning now to FIG. 1E, there is shown yet another embodiment of a medicament container, generally indicated at 100", made in accordance with the principles of the present invention. The medicament container 100" includes an upper layer which is preferentially configured in the same manner as upper layer 104 in FIGS. 1A through 1C and is therefor numbered accordingly.

Disposed adjacent the upper layer 104, the medicament container 100" also includes a middle layer which is preferably configured in the same manner as the middle layer 108 of FIGS. 1A through 1C and is therefore numbered accordingly.

Normally attached to the upper layer 104 and middle layer 108 is a medicament carrying tray. The medicament carrying tray is preferably configured in a manner similar to the medicament carrying tray 186 of FIG. 1D and is, therefore, numbered accordingly. As with the embodiment in FIG. 1D, the medicament carrying tray 186 is preferably formed of a semi-rigid material, such as polyvinyl chloride (PVC), polyvinyl dichloride (PvdC), or fluoronated and/or chloronated homopolymers/copolymers (Aclar), and has a plurality of concave receptacles 192 formed therein.

Disposed below the medicament carrying tray 186 is a lower layer 112 which, as shown in FIG. 1E, is formed by the disk 156 discussed in FIGS. 1A through 1D. The receptacles 164 in the disk 156 are preferably sized to receive the receptacles 192 of the medicament carrying tray 186 so that the upper layer 104, the middle layer 108 and the medicament carrying tray can be securely attached to the disk 156 forming the lower layer 112. The disk 156 forming the lower layer 112 protects the remaining structures and makes the medicament container 100" much stronger and resistant to damage than the prior art blister packs currently used.

In light of the discussion with respect to FIGS. 1A through 1D, those skilled in the art will appreciate that there are several desirable configurations for the medicament container. For simplicity, the remainder of the application, except where specifically noted, uses the medicament container 100 shown in FIGS. 1A through 1C. It should be appreciated that the medicament containers 100' (FIG. 1D) and 100" (FIG. 1E) could also be used with the same highly advantageous results.

In a similar manner to the embodiment shown in FIG. 1D, the upper layer 104, the middle layer 108 and the medicament carrying tray 186 can be attached together as an integral unit which is sold or distributed separately from the lower layer 112. In such a configuration, the lower layer 112 would typically be permanently disposed in an inhalator housing, and the container formed by the upper layer 104, the middle layer 108 and the medicament carrying tray 186 being nestable in the disk 156 forming the lower layer.

Figure 2A:
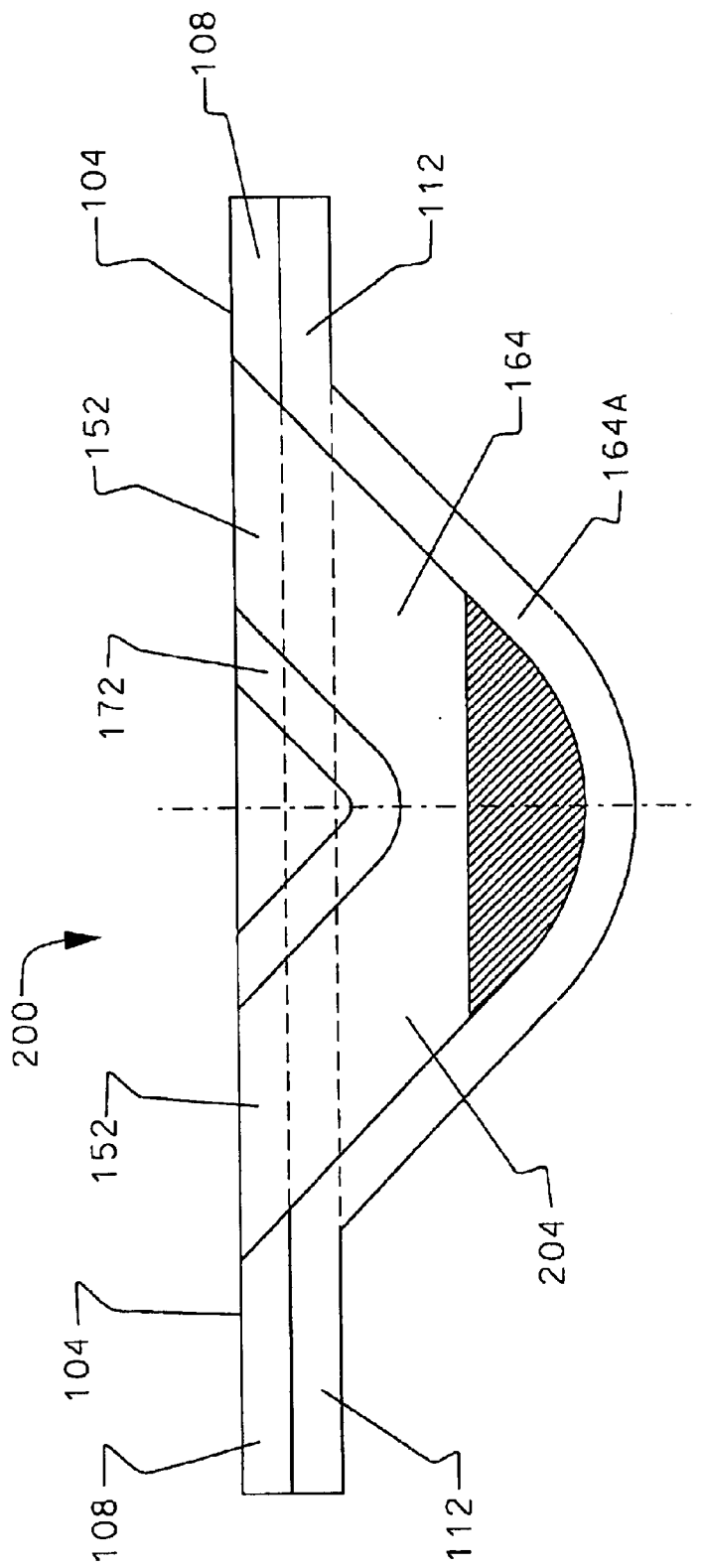
FIG. 2A shows a side cross-sectional view of one blister of a medicament container made in accordance with a preferred embodiment of the present invention.

FIG. 2A shows a side cross-sectional view of one blister of the medicament container 100 made in accordance with a preferred embodiment of the present invention. The blister, generally indicated at 200, is formed by the upper layer 104, the middle layer 108 and the bottom layer 112.

The upper layer 104 forms a top covering to the blister 200. Below the upper layer 104, the openings 152 in the middle layer 108 and the receptacle 164 defined by the generally triangular recess in the bottom layer 112 form a medicament containment area/flow channel 204. The upper side of the medicament containment area/flow channel 204 is defined by the triangular projection 172 of the middle layer 108 which extends below the upper surface of the bottom layer (represented by dashed lines 112a). The bottom side of the medicament containment area/flow channel 204 is defined by the triangularly recessing wall 164a of the bottom layer 112. As defined between the projection 172 and the wall 164a, the medicament containment area/flow channel 204 is generally elbow shaped, but may be other shapes as well.

Medicament contained in the medicament containment area/flow channel 204 tends to remain at the bottom of the triangular receptacle 164 and below the lowermost point of the projection 172 so that an airflow path is maintained within the blister 200. As will be shown momentarily, the medicament is also maintained sufficiently below the upper layer 104 such that when the foil or paper of the upper layer is pierced, it is moved out of the way without engaging the medicament which is in the bottom of the receptacle. Thus, the risk that the medicament will become trapped by pieces of foil is significantly reduced, as the triangular shape tends to concentrate the medicament in the center of the medicament containment area 204.

Figure 2B:
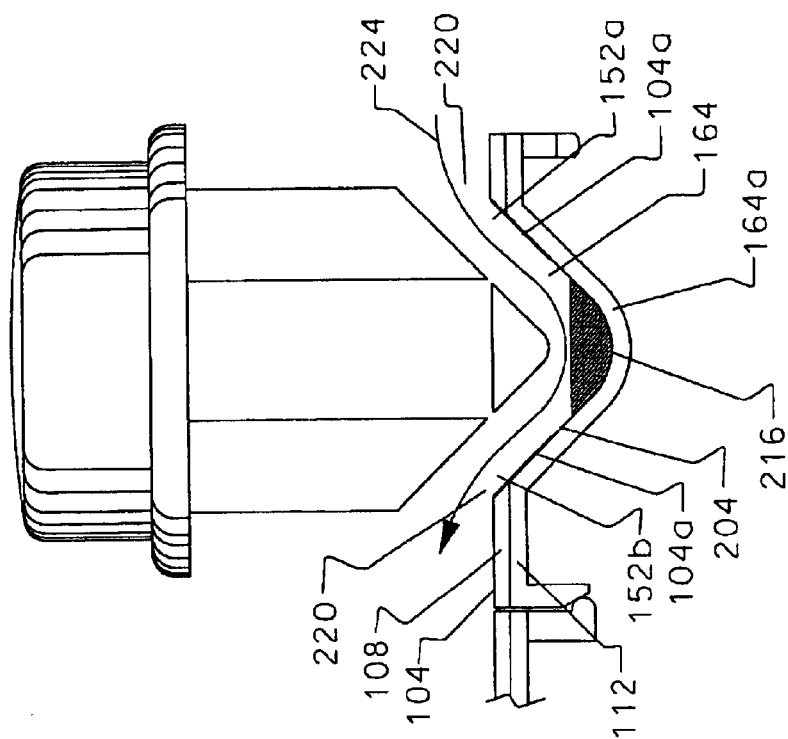
FIG. 2B shows a side cross-sectional view similar to that of FIG. 2A with the lancet piercing the upper layer of the blister.
Figure 2C:
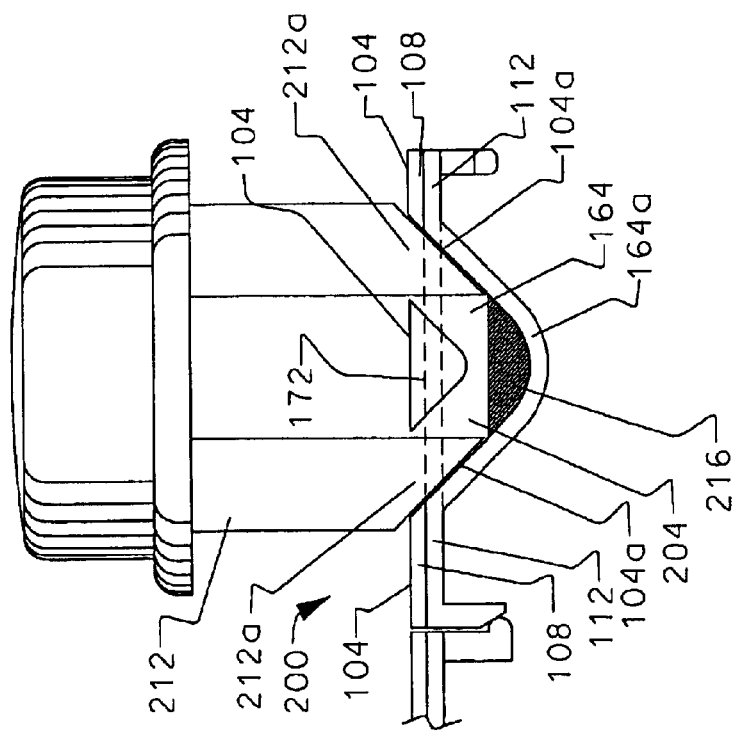
FIG. 2C shows a side cross-sectional view similar to that shown in FIGS. 2A and 2B with a lancet removed from and positioned immediately above the blister.

Turning now to FIGS. 2B and 2C, there are shown side cross-sectional views of the blister 200 similar to that shown in FIG. 2A. In FIG. 2B, a lancet 212 has been moved down so that tapered ends 212a of the lancet have pierced the upper layer 104 of the medicament container 200. As the lancet 212 is driven downwardly, the tapered ends 212a force the foil, etc., from the upper layer 104 into contact with the upper surface of the wall 164a defining the receptacle 164. This pierced material 104a remains against the wall 164a (due to the foil being sheared and bent past its yield point) where it provides almost no interference to entrainment or flow of the medicament 216 in the medicament containment area/flow channel 204. (Of course, in embodiments using a medicament carrying tray 186 (FIGS. 1D and 1E) the foil is pressed against the walls of the receptacles 192 rather than directly against the lower layer. As used herein, descriptions of pressing the foil against the lower layer should he construed as including pressing the foil against the receptacle of the medicament tray when a medicament tray is included).

In FIG. 2C, the lancet 212 has been withdrawn from the blister 200 to leave two holes 220 on the same side of the medicament container, but at opposing ends of the medicament containment area/flow channel 204. Extending between the two holes 220 is an elbow-shaped channel which provides a flow path through the upper layer 104, through one 152a of the openings 152 in the middle layer 108, through the receptacle 164 defined by the lower layer 112, back through the other opening 152b and out of the blister 200.

The airflow channel, represented by airflow 224, is further defined by the tapered ends 212a of the lancet 212. When the lancet 212 is withdrawn from the blister, the tapered ends 212a channel airflow into the blister and help direct airflow coming out of the blister.

In accordance with the present invention, it has been found that the elbow-shaped configuration, formed by the projection 172 of the middle layer 108 and the wall 164a defining the receptacle 164 in the bottom layer 112, provides significantly improved entrainment of the medicament as air flows through the medicament containment area/flow channel 204. Unlike a conventional configuration in which the airflow is traveling through holes in opposing sides of the blister and may not entrain medicament which is disposed in the more lateral portions of the blister, the airflow of the present configuration impacts the medicament 216 along a curved path which maximizes entrainment. Thus, it has been found that the configuration shown in FIG. 2C provides more consistent medicament delivery.

Figure 2D:
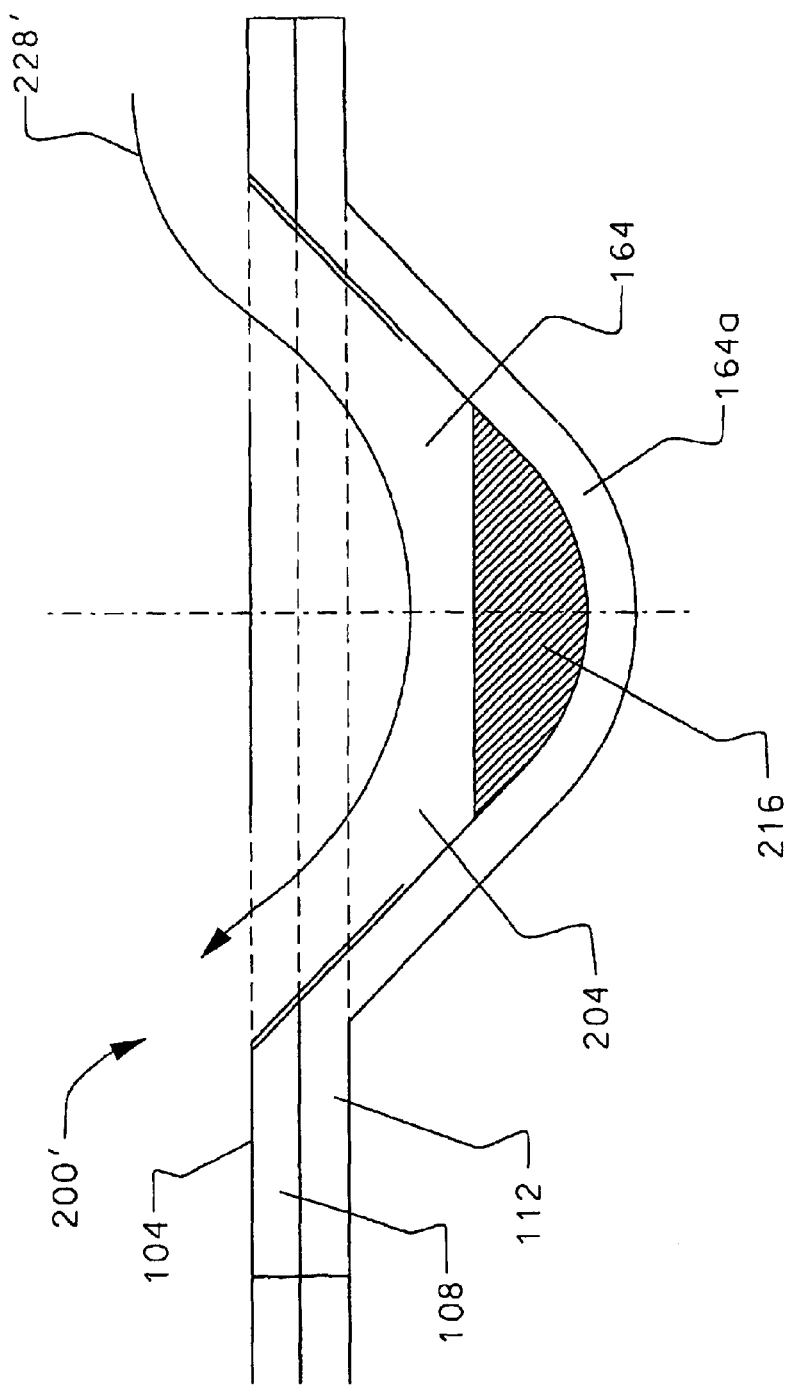
FIG. 2D shows a side cross-sectional view of another embodiment of the present invention wherein the middle layer has been omitted.

Turning now to FIG. 2D, there is shown a blister 200' made in accordance with another aspect of the present invention. The blister 200' preferably includes the upper layer 104, the middle layer 108 and the bottom layer 112. Unlike the configuration discussed in FIGS. 1A through 2C, however, the blister 200' does not have a projection 172 which extends into the medicament receptacle 164. Thus, a triangular medicament containment area/flow channel 204' is defined by the upper surface of the wall 164a and the lower surface of the upper layer 104. (Of course, the middle layer could be omitted if desired.)

When the upper layer 104 is punctured, the triangular flow channel 204' is opened and air is able to flow through the blister 200' as demonstrated by arrow 228'. The triangular airflow channel 204' is generally less efficient at entrainment of medicament than the elbow-shaped medicament containment area/flow channel 204 formed by the projection (FIGS. 2A through 2C) because the airflow is not concentrated against the medicament 216 to the same degree. However, the triangular air flow channel 204' is still a marked improvement over conventional blister configurations in which the blister is punctured through the top and bottom of the blister.

Figure 3A:
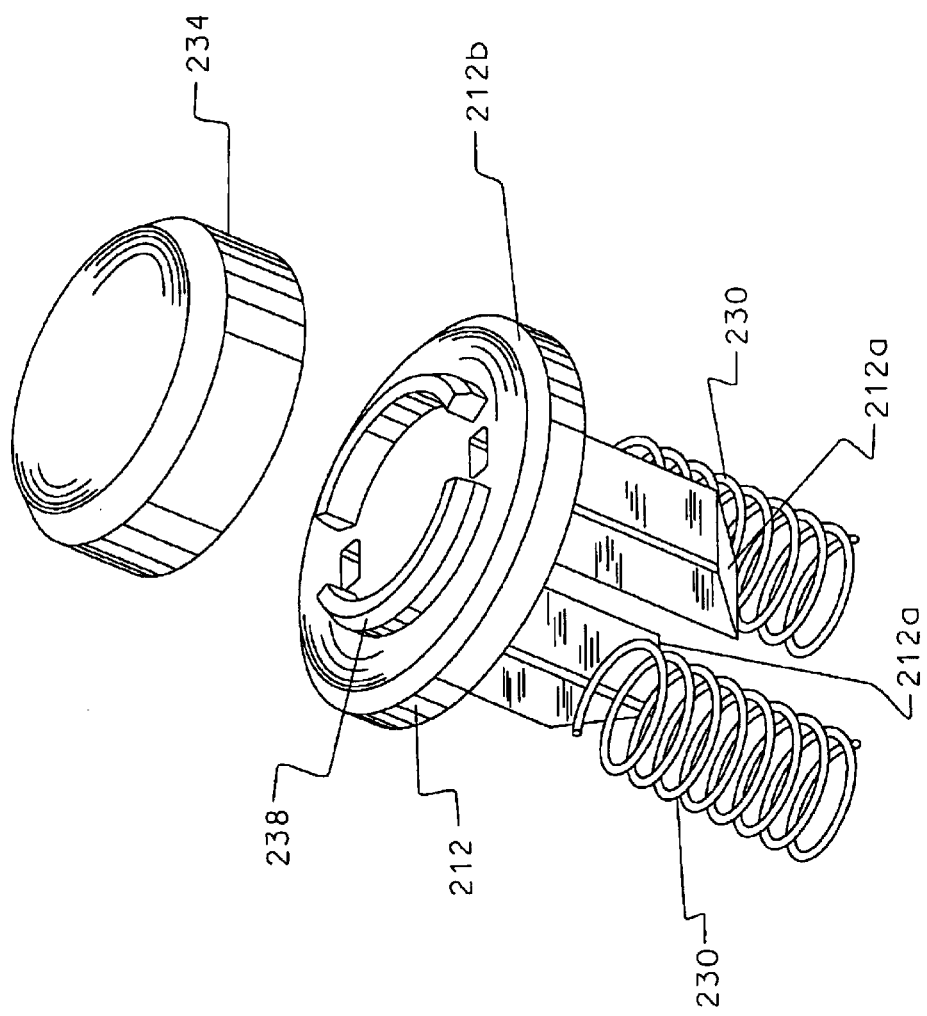
FIG. 3A shows an exploded view of a lancet mechanism made in accordance with the principles of the present invention.
Figure 3B:
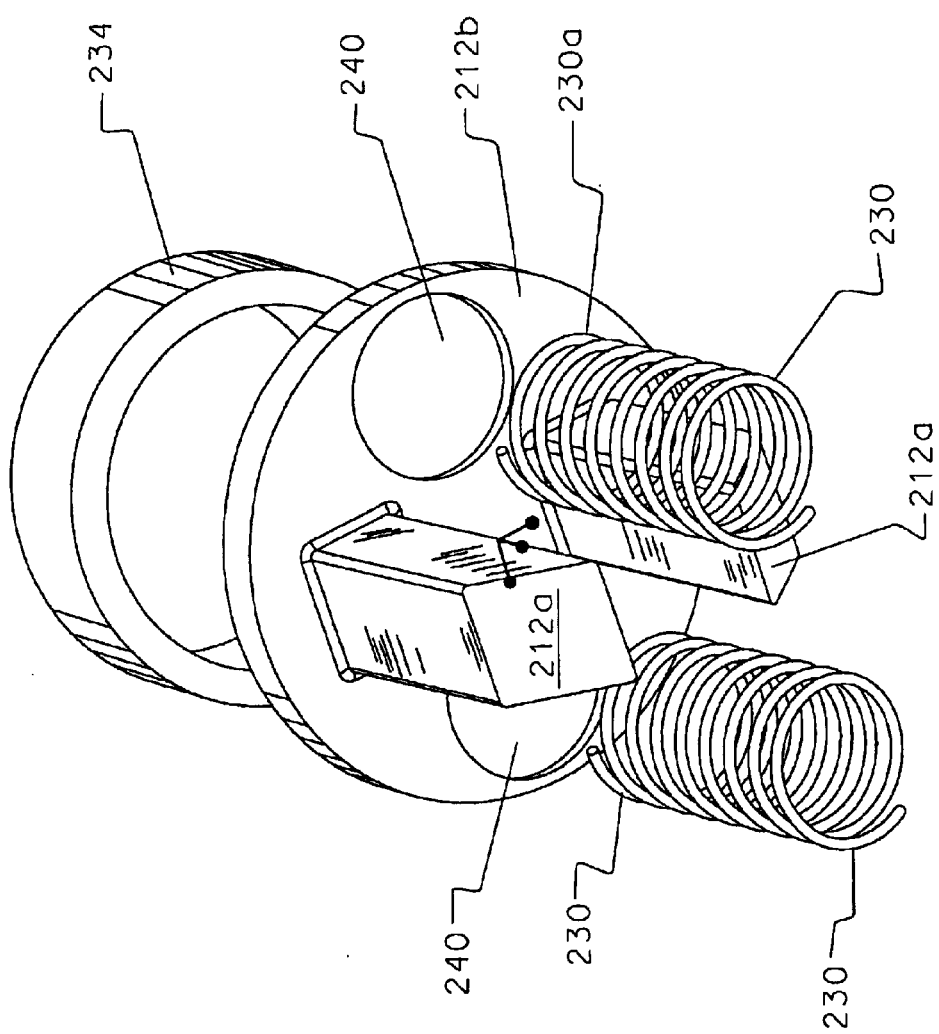
FIG. 3B shows a bottom exploded view of the lancet mechanism of FIG. 3A.

Turning now to FIGS. 3A and 3B, there are shown exploded views of a lancet mechanism 212 made in accordance with the principles of the present invention. To puncture the medicament container 100, the lancet 212 has a pair of tapered ends 212a which are preferably tapered at an angle similar to the angle of the wall 164a which defines the receptacle 164 (FIGS. 1B through 2D). One or more springs 230 are provided to bias the lancet 212 away from the blister 200.

To actuate the lancet 212, a button 234 at the top of the lancet body 212b is depressed. While shown as a separate piece which mates with a flange 238 for attachment, the button 234 could be integrally formed with the other portions of the lancet 212.

FIG. 3B shows a bottom exploded view of the lancet mechanism 212. As shown in FIG. 3B, the button 234 is preferably hollow to receive the flange (238 in FIG. 3A) disposed at the top end of the lancet body 212b. Furthermore, a pair of recesses 240 are preferably formed toward the top of the lancet body 212b to receive the upper end 230a of the springs 230.

Figure 4:
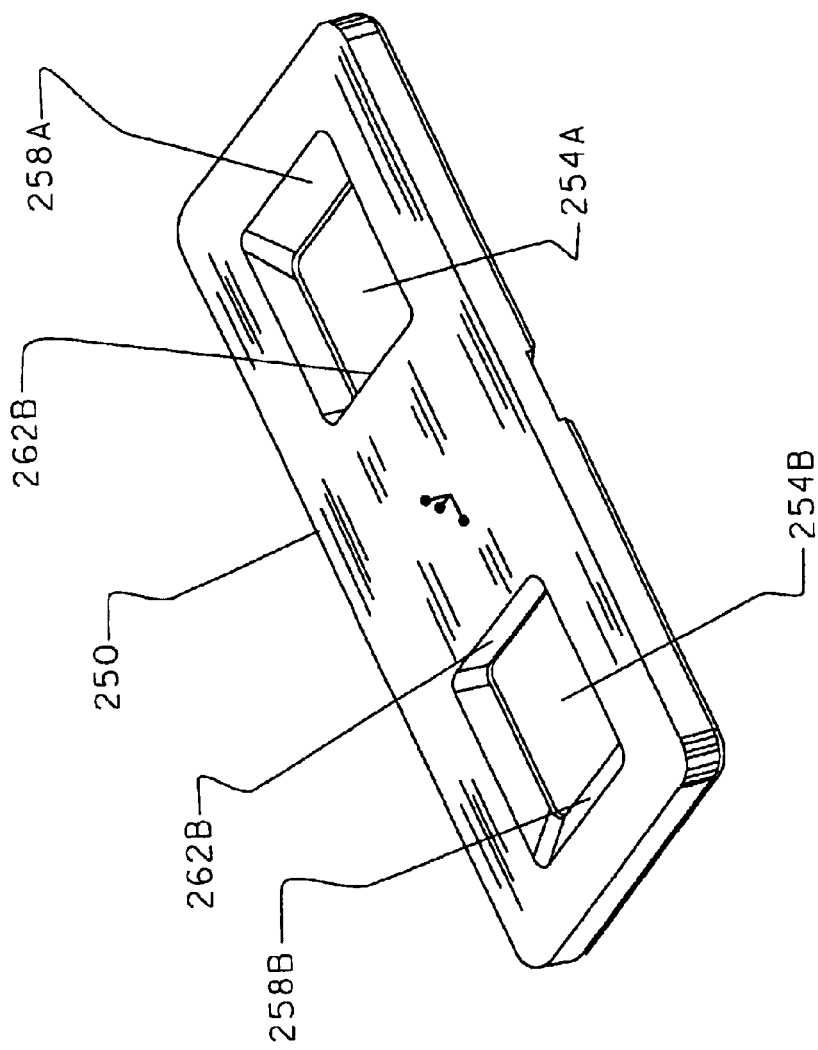
FIG. 4 shows a perspective view of a sealing member formed in accordance with the principles of the present invention.

Turning now to FIG. 4, there is shown a perspective view of a sealing member, generally indicated at 250, formed in accordance with the principles of the present invention. The sealing member 250 is configured for placement above the blister 200 which is to be opened to improve airflow through the medicament containment area/flow channel 204 (FIGS. 2A thorough 2D). The sealing member 250 is typically made from a rectangular piece of semi-resilient material, such as silicone rubber.

The sealing member 250 includes a first opening 254a and a second opening 254b. The first and second openings 254a and 254b are spaced apart and configured for alignment with the holes 220 (FIG. 2C) disposed at either end of the medicament containment area/flow channel 204 of the blister 200. Thus, the openings 254a and 254b extend the airflow channel formed by the medicament containment area/flow channel 204 and limit leakage.

The openings 254a and 254b in the sealing member 250 are preferably provided with a beveled or angled outer sidewall 258a and 258b which is configured for alignment with the wall 164a forming the receptacle 164 (FIGS. 1A through 2C). The opposing sidewall 262a and 262b may be parallel to the outer sidewall.

Figure 4A:
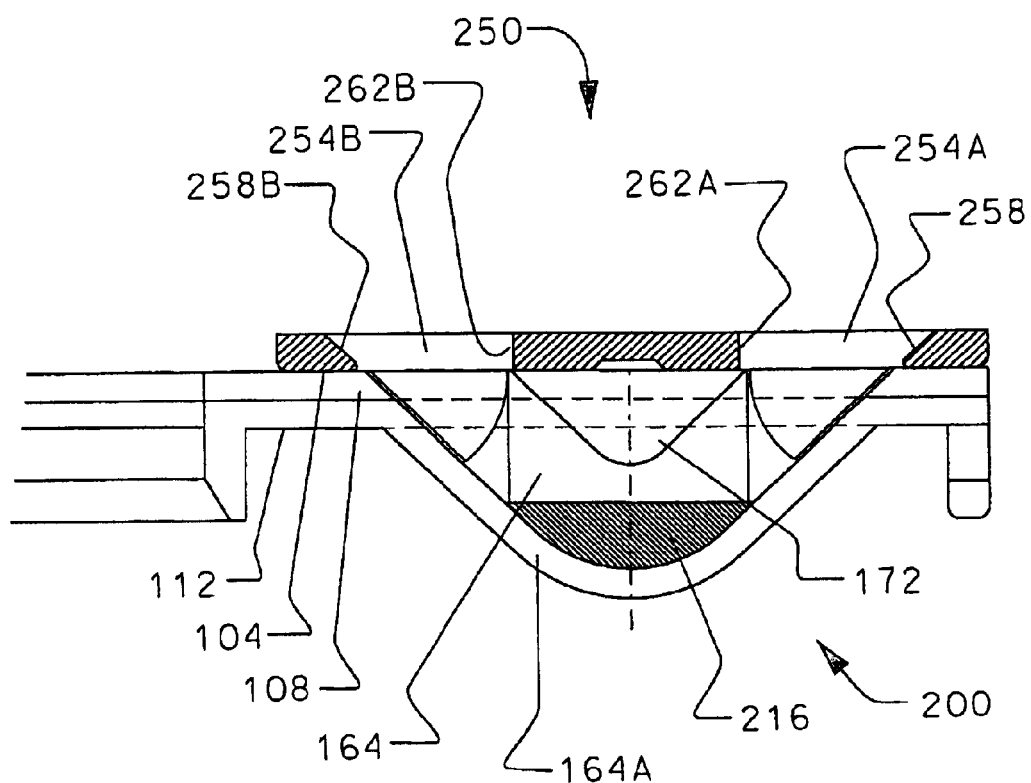
FIG. 4A shows a side cross-sectional view of a blister and sealing member positioned adjacent one another in accordance with the principles of the present invention.

As shown in FIG. 4A, the angled sidewalls 258a and 258b of the sealing member 250 are disposed in alignment with the wall 164a forming the receptacle 164 so as to form a generally continuous wall from the opening 254a, through the medicament containment area/flow channel 204, and to the opening 254b. Thus, the angled openings 254a and 254b channel airflow smoothly into the medicament containment area/flow channel 204 of the blister 200.

Figure 5A:
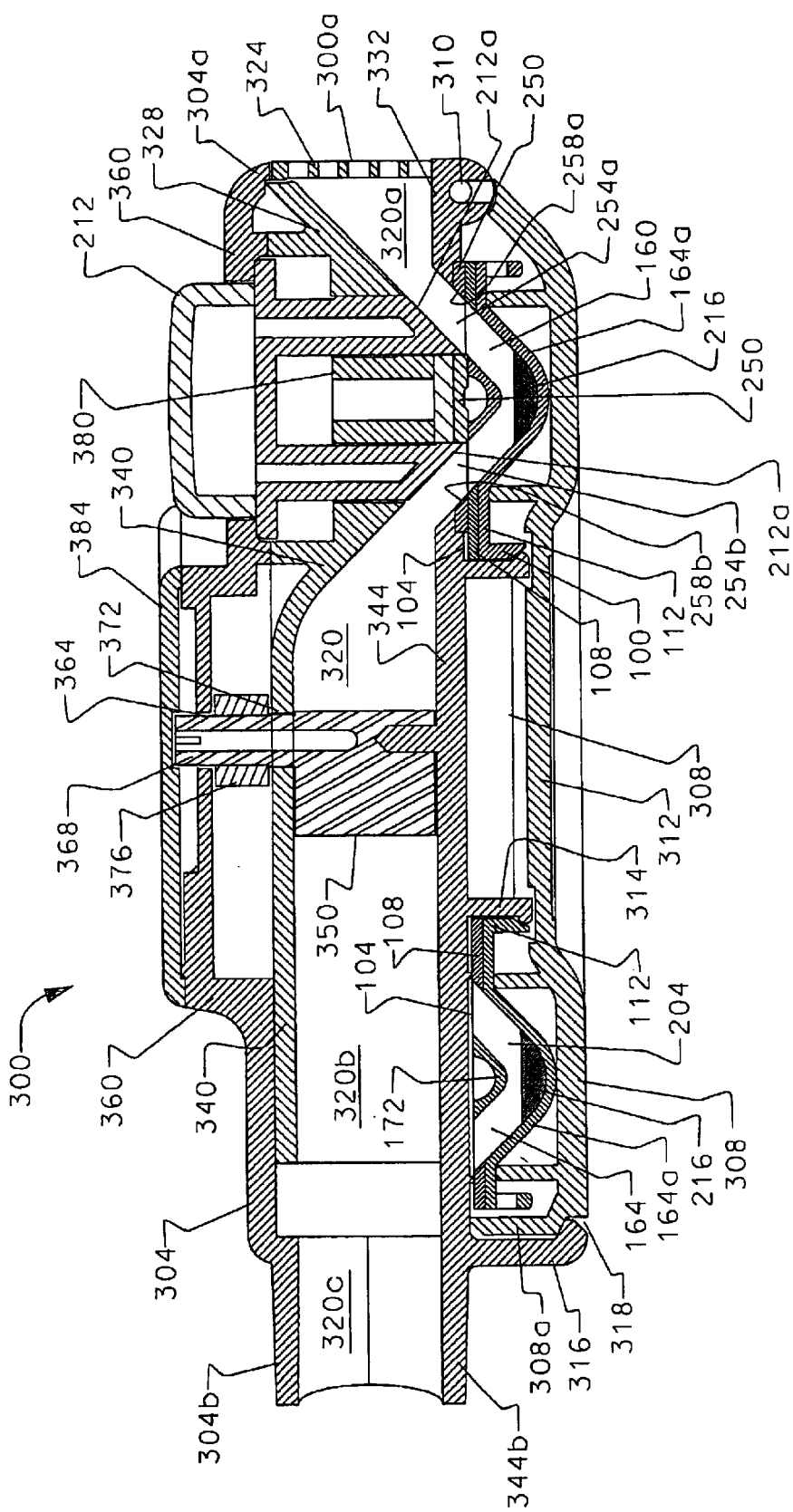
FIG. 5A shows a cross-sectional view of a housing formed in accordance with the present invention for receiving a medicament container, the housing being configured with the lancet in a resting position prior to piercing of the medicament container.

Turning now to FIG. 5A there is shown a cross-sectional view of a housing, generally indicated at 300, formed in accordance with the present invention. The housing includes an upper, airflow portion 304, and a lower, medicament receiving portion 308, which are preferably attached to one another by a hinge 310 disposed at the distal end 300a of the housing 300.

The hinge 310 allows a wall 312 of the lower portion 308 to pivot away from the upper portion 304 to expose a cylindrical collar 314 which extends downwardly from the upper portion 304. The cylindrical collar 314 is substantially the same size as the opening 160 in the medicament container 100 so that the medicament container can be mounted on and rotated about the collar as shown in FIG. 5A.

Once the medicament container 100 is mounted on the cylindrical collar 314, the wall 312 is pivoted back toward the upper portion 304 until a catch 316, which extends downwardly from the upper portion 304, engages a groove 318 along the wall. Once the catch 316 engages the groove 318, the wall 312 is held in a closed position, thereby holding the medicament container 100 in the lower portion 308.

The upper airflow portion 304 defines a medicament airflow channel 320 which extends from a first, distal end 304a to a second, proximal end 304b of the upper portion. A grate 324 is disposed at the first end 320a of the medicament airflow channel 320 to limit entry of foreign bodies into the channel. From the grate 324, the channel 320 is tapered downwardly toward the second, lower portion 308 which houses the medicament container 100. The lancet 212 is disposed adjacent the distal end 320a of the channel 320 so that the tapered end 212a is disposed over the blister 200 disposed in the lower portion 308, and so that the tapered end is in alignment with the wall 328 which defines the tapered portion of the channel 320. Thus, the tapered end 212a helps direct airflow to the blister 200 in the lower portion 308 when the lancet 212 is in a resting position.

The lower side of the channel 320 is formed by a lower wall 332 of the first, upper portion 304, and the angled sidewall 258a of the opening 254a of the sealing member 250. As shown in FIG. 5A, the lower wall 332 extends straight and then angles downwardly parallel to the wall 328 and the tapered end 212a of the lancet 212. Thus, the initial portion 320a of the airflow channel 320 narrows as it approaches the blister 200, thereby increasing the speed of the airflow.

The initial portion of the airflow channel 320a ends at the upper layer 104 of the medicament container 100. Until the upper layer 104 is punctured by the lancet 212, airflow through the channel 320 is prevented. Airflow through the channel 320 once the lancet 212 punctures the upper layer 104 is discussed in detail with respect to FIGS. 5B and 5C below.

The airflow channel 320 continues through the upper portion 304 at the opposing side of the blister 200. The channel 320 continues from the opening 254b in the sealing member 250. As the channel 320 extends proximally from the blister 200, it extends upwardly at an angle. The channel 320 is defined on its upper side by the tapered end 212a of the lancet 212 and by a wall 340 which gradually curves until it is disposed in a horizontal orientation.

The lower side of the channel 320 is formed by the angled sidewall 258b of the sealing member 250 and a wall 344 which has an angled distal end and then extends horizontally. The wall 344 can also form the base for the cylindrical collar 314 and the catch 316.

The positions of the walls 340 and 344 form a channel whose distal portions 320b have approximately the same cross-sectional area as the initial portion prior to narrowing. At a far proximal end 320c, the channel 320 is defined by a generally cylindrical wall 344b which forms a mouthpiece through which the user can inhale.

Disposed along the airflow channel 320 is a rotatable airflow control member 350. As will be discussed in detail in FIGS. 6A through 6C, the airflow control member 350 selectively limits airflow through airflow channel 320 to improve deep lung deposition of the medicament 216 contained in the medicament container 100.

FIG. 5A also shows several other structures which assist in the functioning of the housing 300. The housing 300 includes an upper wall 360. The upper wall 360 holds the walls 328 and 340 in place and helps properly position the lancet 212. The upper wall 360 also has an opening 364 which receives a post 368 of the rotatable airflow control member 350. A similar opening 372 is also formed in the wall 340, and a collar 376 can be disposed around the post 368 between the walls 340 and 360. The housing 300 also includes a support structure 380 which fits between the tapered ends 212a of the lancet 212, and a cap 384 which is disposed above the upper wall 360. The cap 384 keeps dust from entering around the post 368, seals the primary air cavity and contains the spiral torsion spring which creates bias for the air vane 430 discussed below.

Figure 5B:
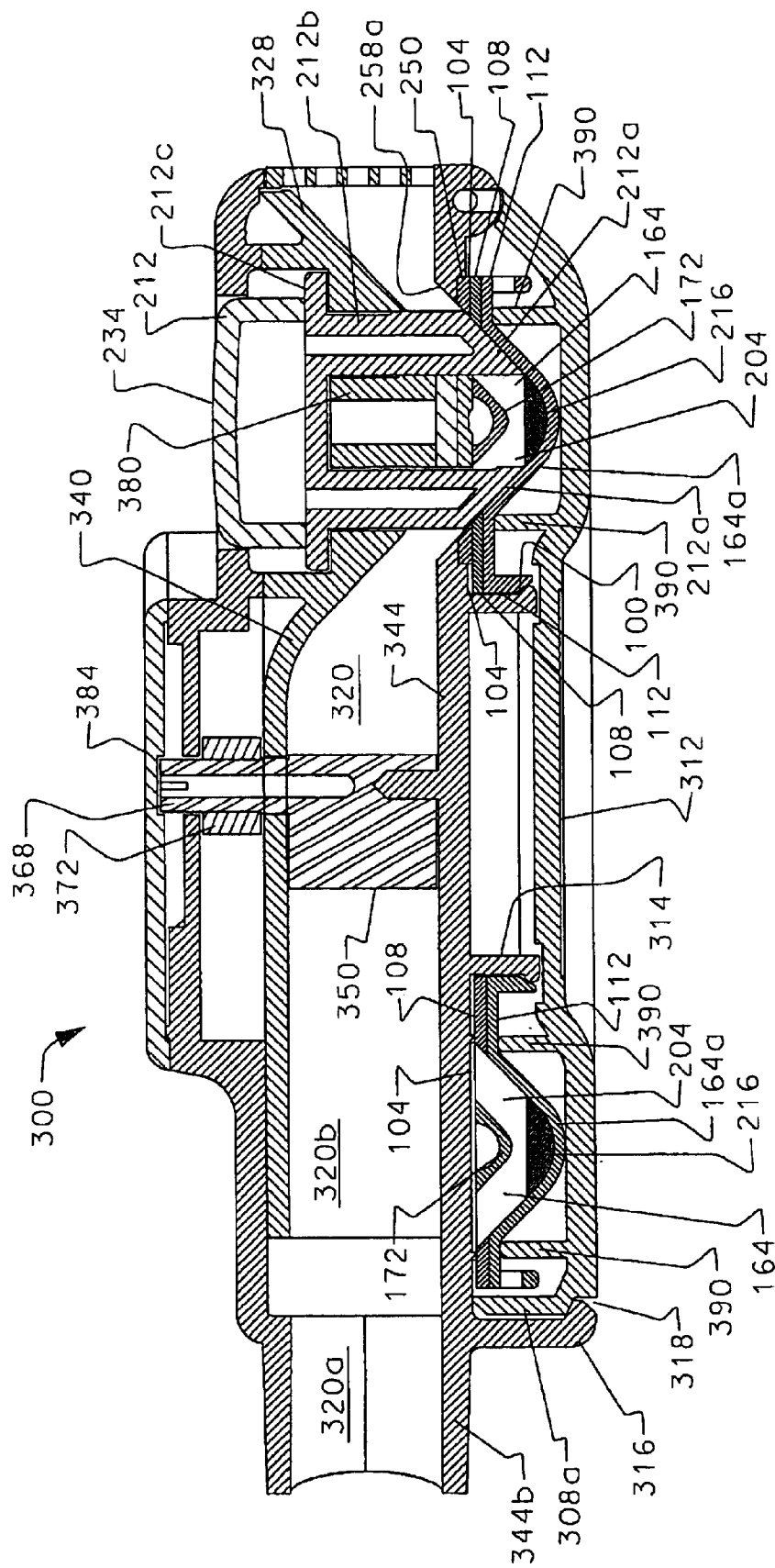
FIG. 5B shows a side cross-sectional view of the housing similar to that of FIG. 5A, but with the lancet being advanced to pierce the upper surface of the medicament container.

Turning now to FIG. 5B, there is shown a side cross-sectional view of the housing 300 similar to that of FIG. 5A. The primary difference in FIG. 5B is that the button 234 of the lancet 212 has been pressed downwardly so that the tapered ends 212a on the opposite end of the lancet are advanced through the upper layer 104 (FIG. 5A) of the blister 200 and into the medicament containment area/flow channel 204. The range of travel of the lancet 212 is limited by interaction between the flange 212c of the lancet body 212b and the upper wall 360 and the walls 328 and 340, and by the upper surface of the lower layer 112.

As the tapered ends 212a of the lancet 212 extend down into the medicament containment area/flow channel 204, the tapered ends shear and/or puncture the upper layer and force the sheared portions of the upper layer 104 against the wall 164a which defines the receptacle 164. Thus, unlike the prior art, the sheared portions of the upper layer 104 are pushed into a position where they provide virtually no interference to airflow through the medicament containment area/flow channel 204, and do not interfere with medicament entrainment.

The medicament container 100 is preferably formed with a bottom layer 112,which is rigid or semi-rigid (as opposed to the flexible foil common in the prior art). The rigidity helps to support the medicament container 100. Further, a pair of support walls 390 preferably extend upwardly from the wall 312 of the lower portion 308 of the housing 300. The support walls 390 provide additional assurance against the medicament containment area/flow channel 204 being compressed during actuation of the lancet 212.

Figure 5C:
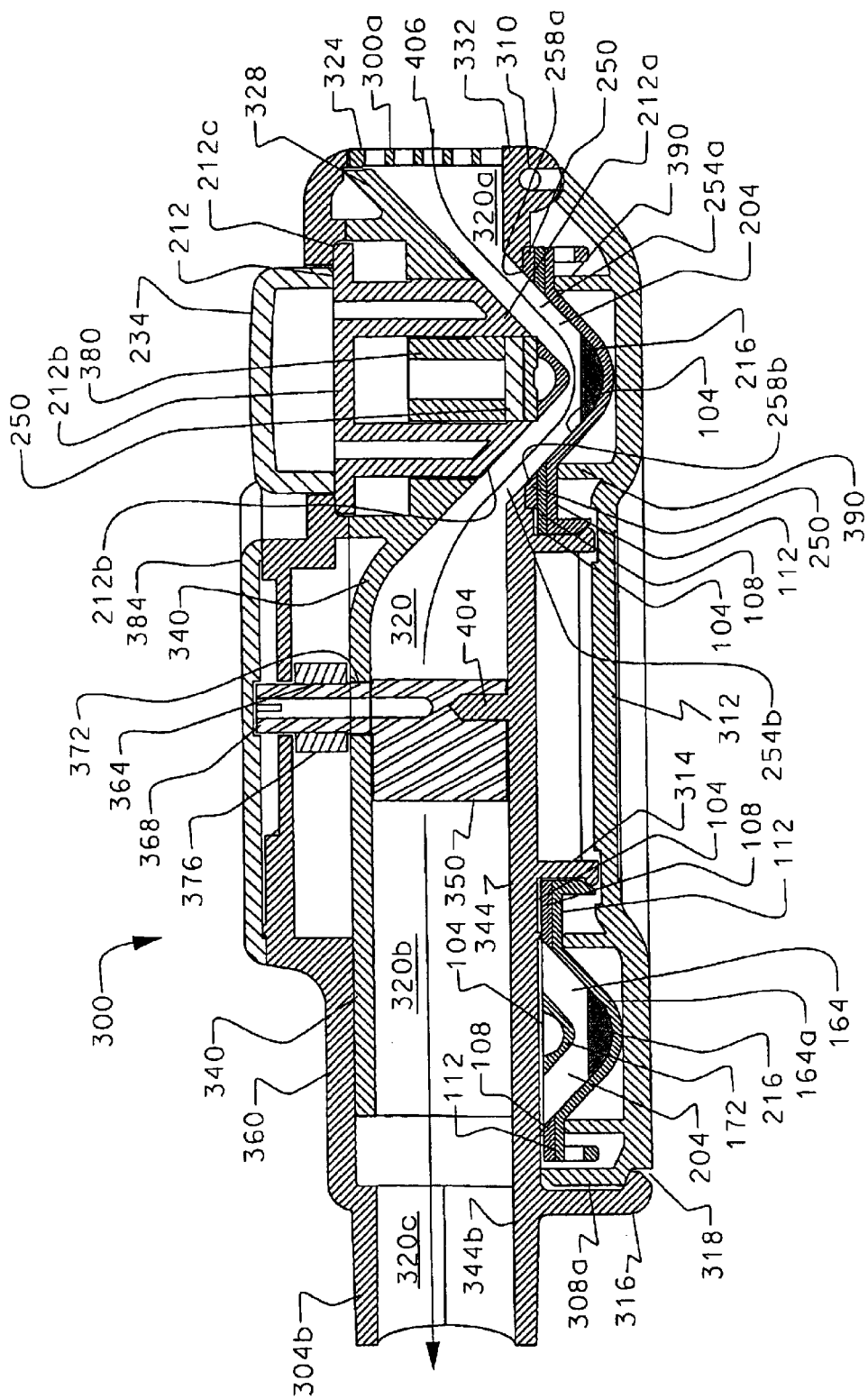
FIG. 5C shows a side cross-sectional view of the housing similar to that of FIGS. 5A and 5B, with the lancet retracted back into a resting position after having pierced the blister of the medicament container.

FIG. 5C shows a side cross-sectional view of the housing 300 similar to that of FIGS. 5A and 5B. In FIG. 5C, the lancet 212 has been returned to its original position. This is accomplished by the springs 230 which are shown in FIG. 3B, but whiff are not visible with the cross-sectional view shown.

With the lancet 212 returned to its original position, the distal most tapered end 212a again is in alignment with the wall 328 to define an upper boundary for the initial portion 320a of the airflow channel 320, and the proximal most tapered end 212a is in alignment with the wall 340 to form a middle portion of the airflow channel. Because the upper layer 104 has been punctured and pressed against the wall 164a forming the receptacle 164, airflow through the medicament containment area/flow channel 204 of the blister 200 is allowed with virtually no interference from the cut portions of the upper layer.

As the air flow passes through the first opening 254a in the sealing member, through the medicament containment area/flow channel 204, and out the second opening 254b of the sealing member, the air follows an elbow-shaped path, as demonstrated by arrow 400. This elbow-shaped path forces the air to engage the medicament 216 at the bottom of the receptacle 164 and results in nearly all of the medicament being entrained in the airflow.

As shown in FIG. 5C, inhaling through the mouthpiece formed by the cylindrical wall 344b in the proximal end 300b of the housing 300 will no instantly cause airflow through the initial portion 320a of the airflow channel 320 and the medicament containment area/flow channel 204. This is due to the airflow control member 350 which pivots about a peg 404 extending upwardly from the wall 344. When the user inhales through the mouthpiece formed by the cylindrical wall 344, the airflow control member 350 initially prevents air from being drawn through the initial portion 320a of the airflow channel and the medicament containment area/flow channel 204. However, as will be explained in detail with respect to FIGS. 6A through 6C, the inhalation by the user causes the airflow contain vane 350 to pivot out of the way, thereby allowing airflow through the airflow channel 320, and specifically through the medicament containment area/flow channel 204.

By delaying airflow through the airflow channel 320 while the airflow control member 350 moves out of the way, the flow of air entrained medicament is delayed momentarily. This allows the user to obtain a predetermined air-flow rate prior to delivery of the medicament, thereby enhancing deep lung deposition of the medicament.

Figure 6A:
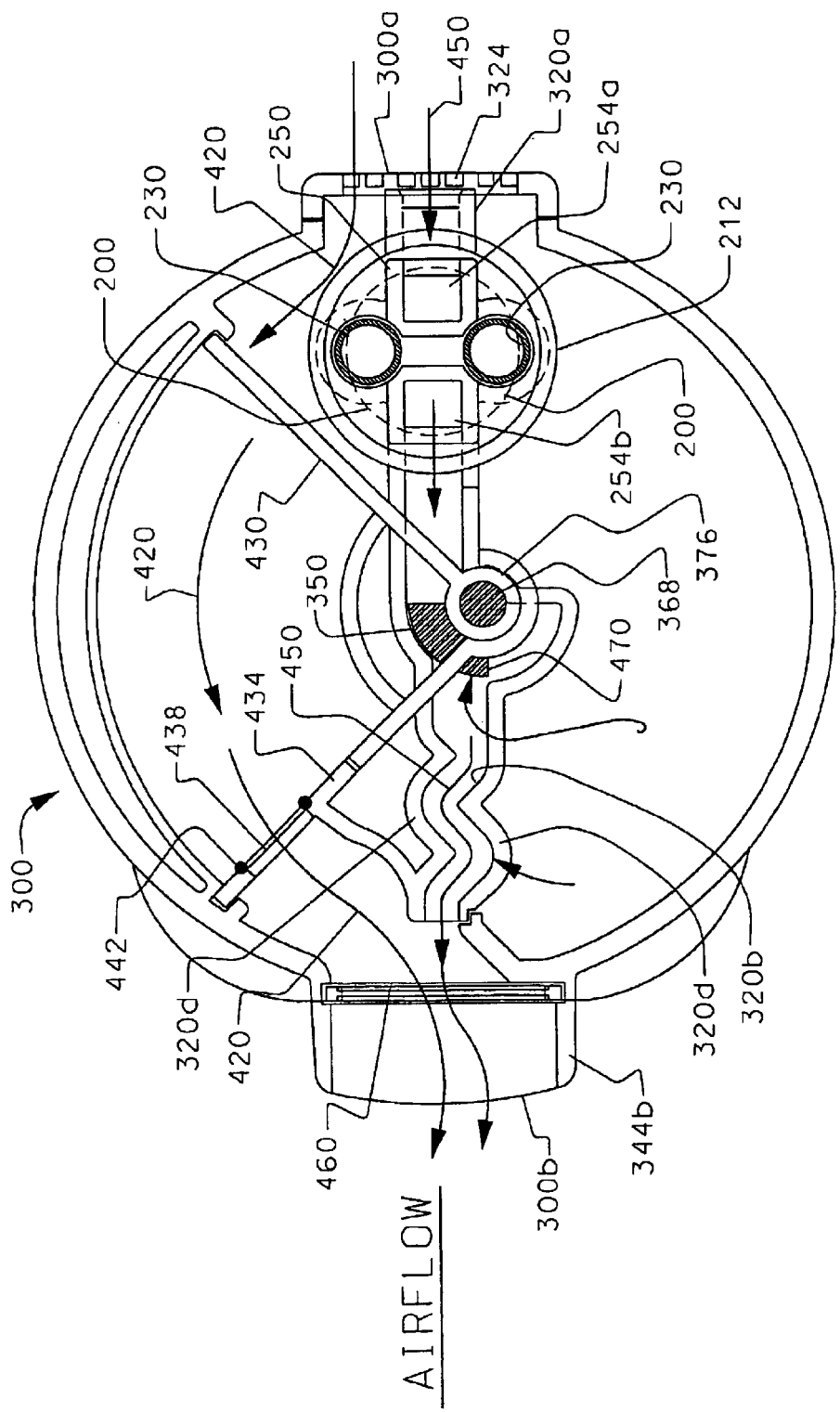
FIG. 6A shows a plan view of several of the internal components of the housing, including primary and secondary airflow channels, with the housing components in an initial resting state.

Turning now to FIG. 6A, there is shown a plan view of the internal components of the housing 300, in accordance with the principles of the present invention. As mentioned previously, the housing 300 has a distal end 300a (i.e. the end which is positioned away from the patient) and a proximal end 300b through which the patient inhales. Disposed at the distal end 300a is a filter or grate 324. Air passing through the grate 324 follows one of two paths.

Initially, the air will turn toward one side of the housing 300, following a primary airflow path as demonstrated by arrow 420. As air follows the primary airflow path 420, it engages a primary air vane 430. The primary air vane 430 is preferably attached to the collar 376 which is mounted on the post 368. As will be explained in additional detail below, the airflow through the primary airflow path 420 moves the primary air vane 430 between an initial position, shown in FIG. 6A and a final position, shown in FIG. 6C, in which the primary ail vane engages a wall 434 having a opening 438 formed therein. Preferably, a sealing member 442, such as an O-ring, is disposed about the opening for purposes discussed below.

The air flowing through the grate 324 may also follow a secondary flow path 450, which is defined by the airflow channel 320 discussed with respect to FIGS. 5A through 5C. Disposed along the airflow channel 320 is the lancet 212 which is biased in a resting position by a pair of springs 230. Disposed below the lancet 212 is the sealing member 250 and the blister 200. The openings 254a and 254b in the sealing member 250 correspond with the tapered ends (not shown in FIGS. 6A through 6B).

From the opening 254b in the sealing member 250, the channel 320 extends generally linearly until it is obstructed by the airflow control member 350. After the airflow control member 350, the middle portion 320b of the airflow channel 320 follows a winding or zig-zag path. This forms a deagglomeration channel. The deagglomeration channel 320b is configured to break up any large agglomerations of medicament which might be present. Because of their larger weight, such agglomerations are less able to turn suddenly with the airflow. Thus, when the airflow turns suddenly, as represented by arrow 450, large agglomerations will continue moving forward until they forcibly impact the walls 320d defining the deagglomeration channel 320b. The force of impact will generally break up the agglomerations.

From the deagglomeration channel 320b, the medicament passes through a mouthpiece filter 460. The mouthpiece filter 460 stops any agglomerations or foreign bodies which may have made it through the grate 324 of the deagglomeration channel 320b.

As shown in FIG. 6A, vary little airflow will occur through the secondary airflow path 450 (airflow channel 320) because the airflow control member 350 forms a closed airflow control valve 470. Thus, when the user initially inhales through the mouthpiece formed by the wall 344b, airflow through the housing will follow the primary airflow path 420.

As the airflow follows the primary airflow path 420, it will move the primary air vane 430 toward the wall 434. Only a relatively small amount of air is able to go around the primary air vane 430 because of an arcuate wall 474 which extends along the arcuate path of the primary air vane. Thus, forceful inhalation is not required to move the primary air vane 430.

Figure 6B:
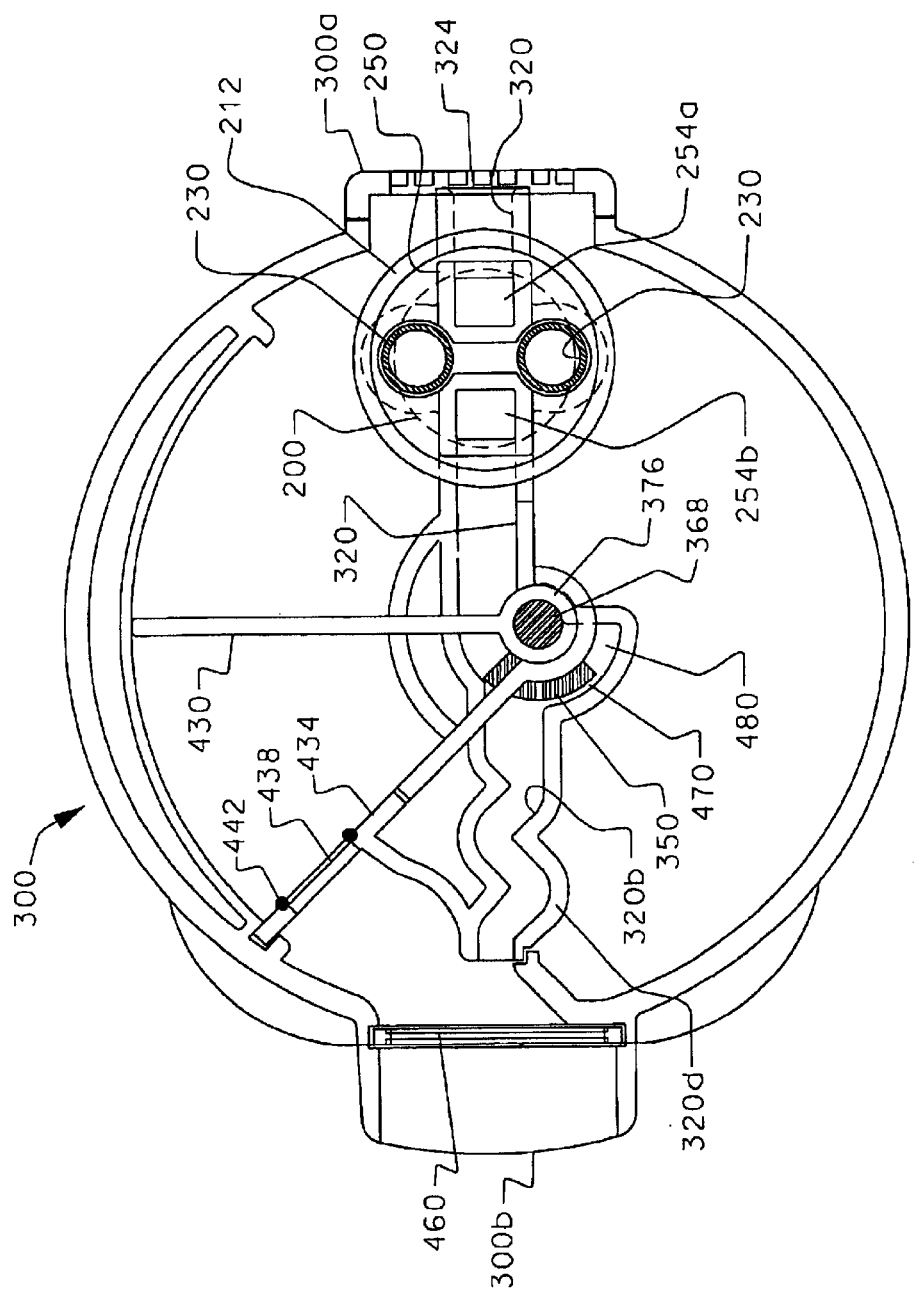
FIG. 6B shows a plan view of the housing similar to FIG. 6A, with the housing components in a middle configuration, in which airflow through both the primary and secondary airflow channels is partially enabled.

As shown in FIG. 6B, the primary air vane 430 has been moved approximately half way (or 45 degrees) from the initial position shown in FIG. 6A to the wall 434. A 45 degree movement of the primary air vane 430 causes a like movement in the airflow control member 350 which forms the airflow control valve 470 in the airflow channel 320. The airflow control member 350 recedes into a channel 480. Thus, by the time the primary air vane 430 is at the half-way point between its initial position and final position, a very small amount of air is able to be drawn through the airflow channel 320.

Figure 6C:
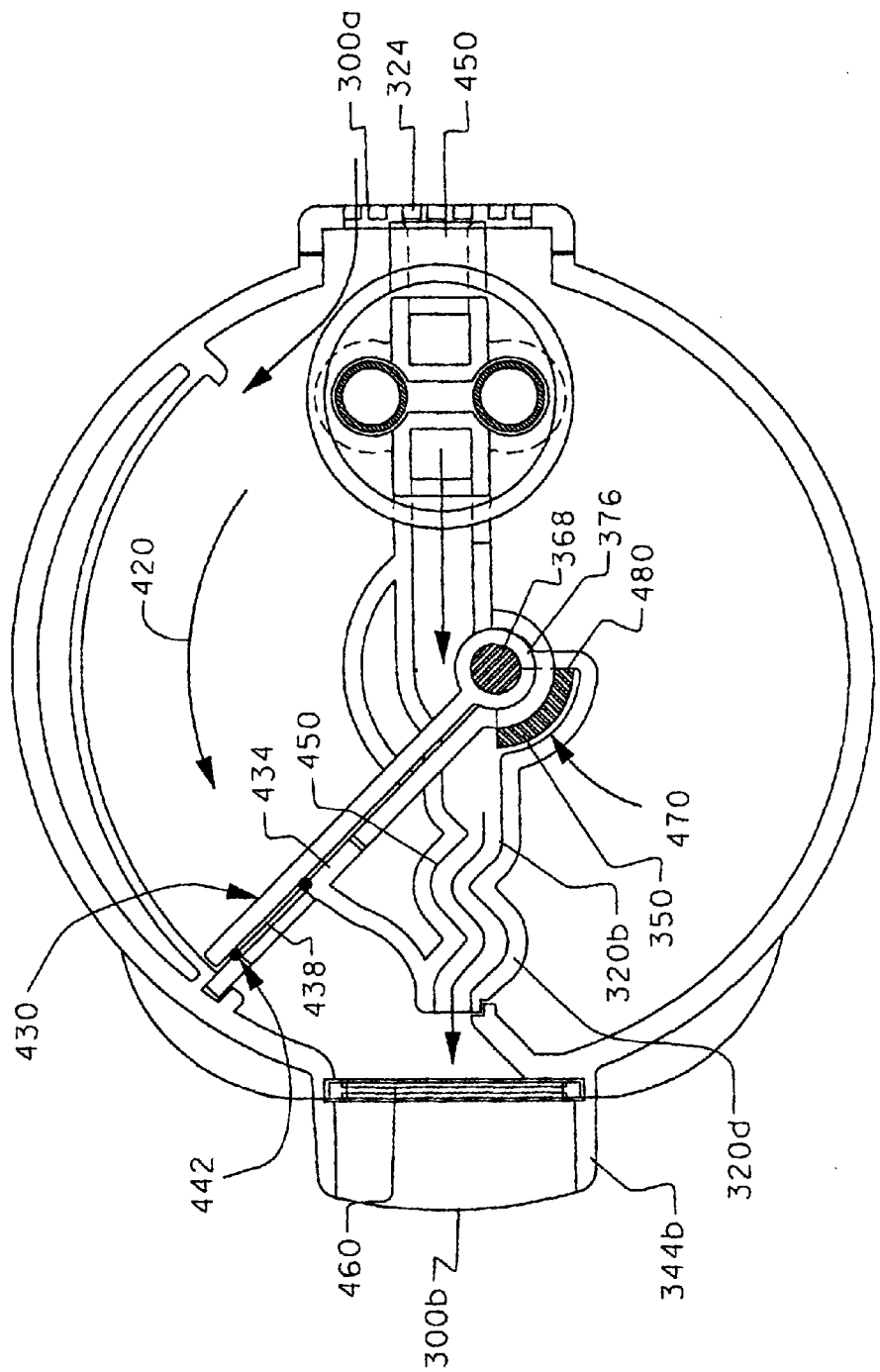
FIG. 6C shows a plan view of the housing similar to FIGS. 6A and 6B, in a final position in which airflow is exclusively through the secondary airflow channel.

As the user continues to inhale through the mouthpiece formed by wall 344b, the primary air vane 430 pivots into its final, closed position shown in FIG. 6C. In the final, closed position, the primary air vane 430 engages the sealing member 442 disposed about the opening 438 in the wall 434 and prevents further airflow through the opening. Thus, once the primary air vane 430 is in the final position, airflow through the primary airflow path 420 is terminated.

Movement of the primary air vane 430 into the final, closed position, also moves the air control member 350 completely into the channel 480, thereby fully opening the air control valve 470. With the primary airflow path 420 fully closed, and the secondary air path 450 fully open, all further inhaled air travels through the airflow channel 320. The airflow entrains the medicament 216 in the blister 200 and carries it to the user. Because of the time required for movement of primary air vane 430 from the initial position (FIG. 6A) to the final position (FIG. 6C), the user is able to achieve a predetermined inhalation rate and his or her lungs are partially inflated before the airflow through the airflow channel 320 carries medicaments to the user's lungs. This increases deep lung penetration of the medicaments and increases their efficacy for those suffering from asthma, etc.

In addition to allowing partial lung inflation prior to the release of medicament, the momentary delay in airflow occurring through the secondary airflow path 450 (i.e. the airflow channel 320) also increases the flow rate of the airflow prior to its initial engagement with the medicament. The increased velocity of the airflow further helps to entrain the medicament in the medicament containment area/flow channel 204 as the air flows therethrough and to deagglomerate larger particles by particle/particle interaction and impacting against the impact surfaces.

Once the user stops inhaling, the primary air vane 430 returns to its initial position. This can be effected by having the primary air vane 430 being spring biased into the initial position, or by simply constructing the housing such that the weight of the primary air vane or the airflow control member 350 causes the two structures to return to the positions shown in FIG. 6A.

Figures 7A, 7B:
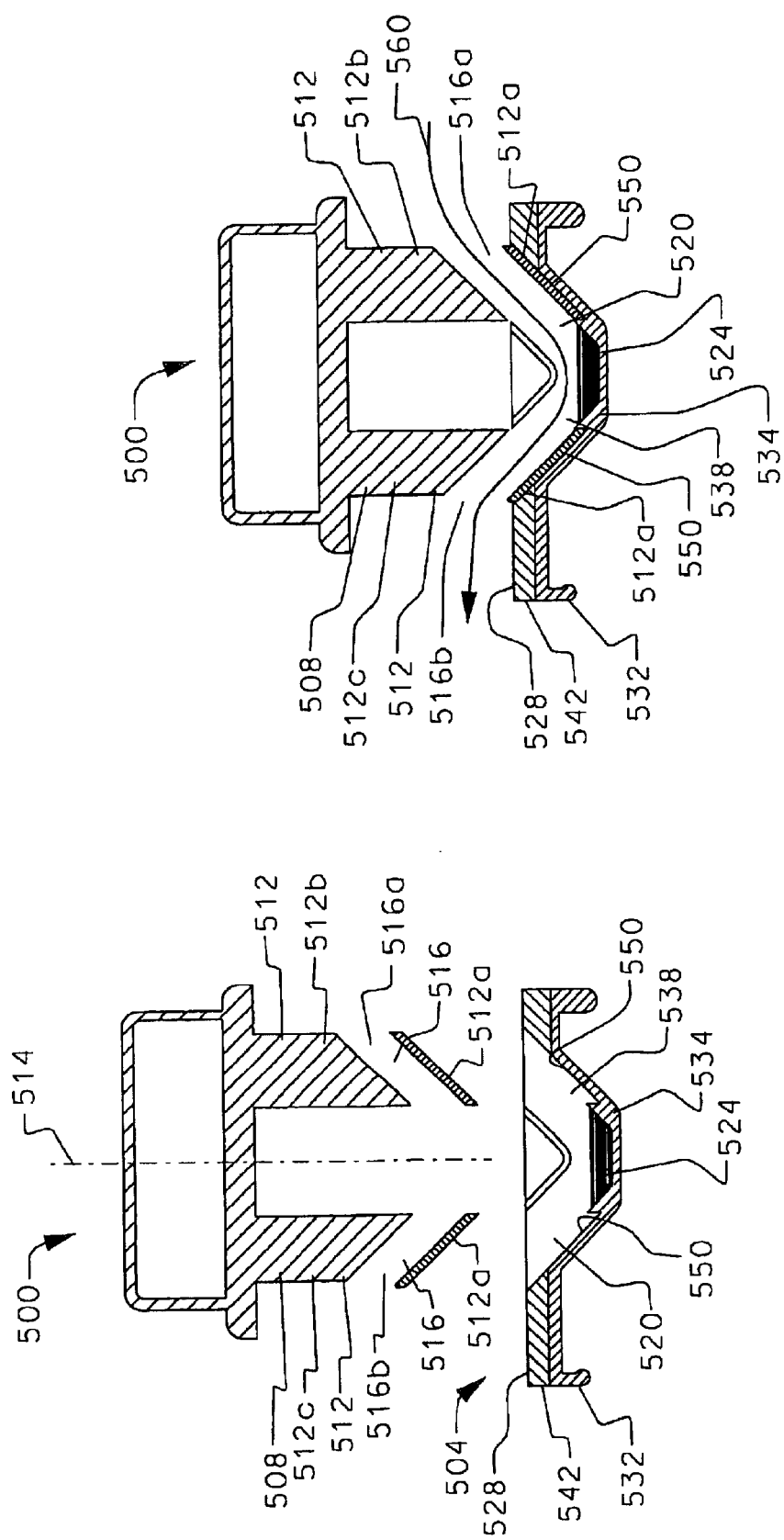
FIG. 7A shows a cross-sectional view of an alternate embodiment of a blister and lancet configuration with the lancet in a resting position prior to piercing of the medicament container.
FIG. 7B shows a side cross-sectional view of the blister and lancet configuration of FIG. 7A with the lancet being advanced to pierce the upper surface of the medicament container.

Turning now to FIG. 7A, there is shown a cross-sectional view of a lancet, generally indicated at 500 and a blister, generally indicated at 504. The lancet 500 includes a body 508 which has two prongs 512 which extend generally parallel to one another. At the bottom of the prongs 512 are a pair of tapered ends 512a. Preferably, the tapered ends 512a each taper toward a longitudinal center axis 514 of the lancet 500.

Unlike the tapered ends 212a of the lancet 212 discussed in FIGS. 3A and 3B, each prong 512 has a channel 516 disposed therein adjacent the tapered end 512a. In the normal orientation of the lancet 500, the proximal prong 512b has a channel 516a which extends downwardly at an angle, typically between about 30 and 45 degrees, as it extends toward the axis 514. (Of course, the channels could be disposed at an angle less than 30 degrees or greater than 45 degrees.) The distal prong 512c, has a channel 516b which extends upwardly and proximally (i.e., toward the user) away from the axis 514 in a similar orientation.

As with the blister 200, the blister 504 has a medicament containment area/flow channel 520 in which medicament 524 is stored. The medicament containment area 520 is defined at an upper extreme by an upper layer 528 which is typically formed of foil or some other readily puncturable material. The bottom of the medicament containment area 520 is defined by a lower layer 532 which has a wall 534 forming a receptacle 538.

A middle layer 542 may be disposed between the upper layer 528 and the lower layer 532. As with the middle layer 108, the middle layer 542 preferably includes a projection 546 disposed in the receptacle 538 to form the substantially elbow-shaped medicament containment area/flow channel 520.

The blister 504 is different from blister 200. While blister 200 is generally triangular in cross-section, blister 504 is trapezoidal. Other configurations could also be used.

FIG. 7B shows a side cross-sectional view of the lancet 500 and blister 504 with the lancet having been advanced from through the first layer 528 and into a second position. In the second position, the tapered ends 512a of the lancet 500 are disposed against the wall 534. Ideally, the portion of the prongs 512 forming the bottom wall defining the channels 516 is disposed in alignment with the upper surface of portion of wall 534 which holds the medicament 524.

With the lancet 500 disposed in the second position shown in FIG. 7B, the channels 516 in the lancet 500 and the medicament container area/flow channel 520, form a portion of an airflow channel represented by arrow 560. Typically, the lancet 500 will be disposed in a housing (such as housing 300) so that channel 516 forms part of the initial portion 320a of the airflow channel 320. To that end, when the lancet 500 is in the second, lower position, the portion of the prong 512 defining the top of the channel 516a is in alignment with the wall (such as wall 328) defining the top of the initial portion of the airflow channel (such as initial portion 320a). Likewise, channel 516b would be in alignment with the channel 320 as it extends from the blister 504 toward the user.

Inhalation by the user causes air to flow through a distal portion of a housing (such as housing 300), through the channel 516a and into the medicament containment area/flow channel 520. The air impacts the medicament 524 and entrains it. The entrained medicament 524 is then carried out the second channel 516b in the lancet 500 and through the remainder of the airflow channel (such as channel 320).

As shown in FIG. 7B, the lancet 500 remains in a second, resting position rather than returning to its original position prior to inhalation by the user. This can be readily accomplished by provided a spring catch which is common on numerous electronic and other devices. When the pressure is applied to the top of the lancet 500, it moves downwardly into the position shown in FIG. 7B and it held in the second position. When pressure is again applied to the lancet 500 it is released and is allowed to return to its original position. Those skilled in the art will be familiar with numerous such spring engagement mechanisms.

While the embodiments above show the use of receptacles 164 and 538 which are either triangular or trapezoidal, in light of the present disclosure, those skilled in the art will appreciate that other cross-sectional shapes could also be used. Thus, the receptacle 164 or 538 could have a cross-sectional shape which is semi-circular, semi-elliptical, etc.

Figure 8A:
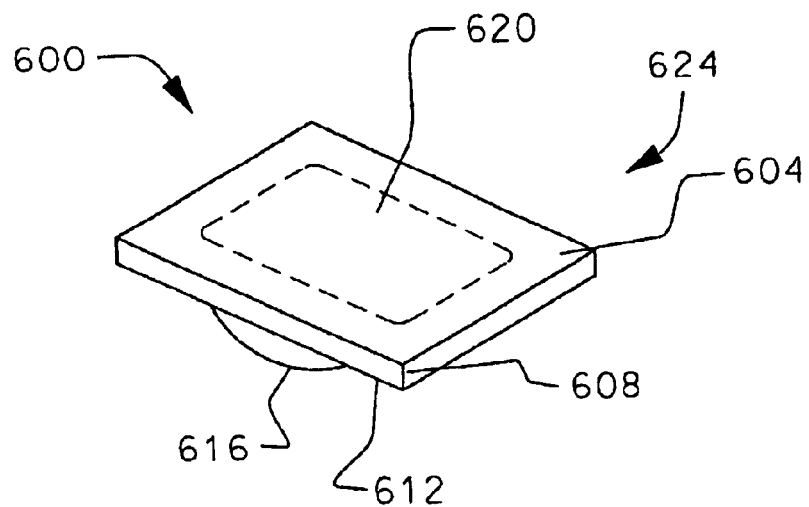
FIG. 8A shows a top view of a blister made in accordance with the present invention.

Turning now to FIG. 8A, there is shown a single blister 600, made in accordance with the principles of the present invention. The blister 600 includes an upper layer 604 which is formed of a readily puncturable or shearable material, such as foil or plastic. The upper layer 604 is supported by a middle layer 608 and a lower layer 612. The middle layer and the lower layer are preferably made of a semi-rigid or rigid plastic or similar material. If desired, the middle layer 608 can be omitted.

As with the previously discussed embodiments, the blister 600 includes a receptacle which is formed by the wall 616 forming the lower layer 612. The receptacle preferably has a generally rectangular opening, indicated at 620 and extends downwardly with a triangular, semi-circular, trapezoidal or semi-elliptical shape. If a projection is used, such as those shown at 172 and 546 (FIGS. 1A and 7B), it is preferred that the projection have a similar cross-sectional configuration as that of the receptacle. Thus, when the receptacle is generally triangular, the projection is preferably generally triangular. By having the bottom surface of the projection extend generally parallel with the upper surface of the wall 616, a smooth airflow path is formed through the blister 600. (Of course, modifications to the relative shapes and configurations of the projection and lower portion could be used to enhance turbulence and medicament entrainment.)

As shown in FIG. 8A, the single blister 600 forms a medicament container, generally indicated 624. Those skilled in the art will appreciate that the housing 300 discussed above could be readily modified to hold a single blister 600. For example, the wall 312 (see FIGS. 5A through 5C) could be shortened so that it simply receives a single blister 600 which is positioned beneath the lancet 212.

Figure 8B:
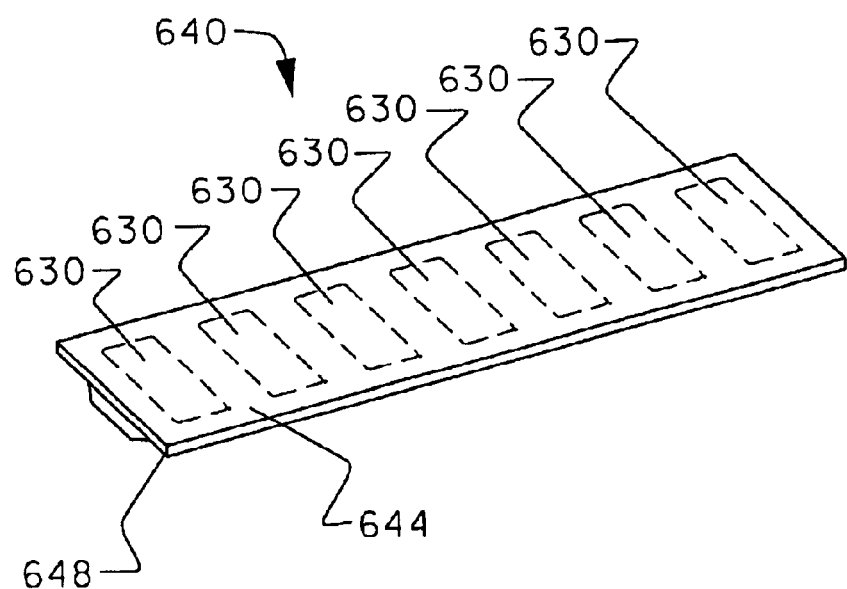
FIG. 8B shows a top view of a linear array of blisters in accordance with the present invention.

In the alternative, the housing 300 (FIGS. 5A through 5C) could be modified to receive blisters, such as those indicated at 630 in FIG. 8B, which are disposed in a linear or rectilinear array 640. After each use, the array 640 is simply advanced one position until all of the blisters have been used.

The blisters 630 are otherwise formed in accordance with the embodiments discussed above, and include at least a readily puncturable or shearable upper layer 644 from a flexible plastic or foil and a semi-rigid or rigid lower layer 648. By semi-rigid, it is meant that the lower layer and the receptacle formed therein will maintain its shape during normal usage. This is in contrast to the prior art foil and flexible plastic medicament containers of the prior art wherein the receptacle can be readily deformed.

The medicament containers disclosed herein provide numerous advantages over the prior art. For example the rigid or semi-rigid lower layer helps maintain the medicament in the desired location and makes the medicament container more durable. By having both holes exit the same side of the blister on opposite ends, the risk of losing medicament if the housing is tipped is reduced. Likewise, not having the medicament fall from the medicament container even after puncturing prevents multiple dosing. Additionally, improved entrainment of the medicament can be achieved, particularly with an elbow-shaped medicament containment area/flow channel in the blister. Furthermore, it is easier to puncture just the upper layer than puncturing through both an upper layer and lower layer of the prior art configurations.

Thus there is disclosed an improved Medicament Container with Same Side Airflow Inlet and Outlet and Method of Use which solves a plurality of disadvantages in the prior art. Those skilled in the art will appreciate numerous modifications which can be made to the embodiments of the invention disclosed herein without departing from the scope and spirit of the present invention. The appended claims are intended to cover such modifications.

What is claimed is:

1. A system for dispensing medicament, the system comprising:
    a housing comprising:
    an airflow channel extending therethrough;
    a portion configured for receiving a medicament container having an upper layer; and
    a lancet disposed in the housing for selectively puncturing or shearing the upper layer of the medicanient container so as to form a first opening and a second opening in the upper layer of the medicament container in alignment with the airflow channel, and
    an airflow control valve disposed along the airflow channel for selectively limiting airflow through the airflow channel.

2. A system for dispensing medicament according to claim 1, wherein the lancet comprises angled ends configured for forcing the punctured or sheared upper layer against the lower layer to minimize interference with medicament entrainment.

3. A system for dispensing medicament according to claim 1, wherein the lancet comprises ends configured for forming a portion of the airflow channel through the housing.

4. The system according to claim 1 wherein the housing further comprises an initial airflow channel having an airflow vane disposed therein.

5. The system according to claim 4, wherein the airflow vane is disposed in communication with the airflow control valve for selectively opening the airflow control valve.

6. The system according to claim 1, wherein the housing further comprises a deagglomeration channel disposed proximally from the airflow control valve.

7. The system according to claim 1, wherein the airflow channel extends in the first opening in the upper layer and out the second opening in the upper layer of the medicament container.

8. A system for dispensing medicament according to claim 1, further comprising a sealing member configured for engaging the medicament container when the medicament container is disposed below the lancet.

9. The system according to claim 8, wherein the sealing member comprises a first opening and a second opening spaced apart from the first opening.

10. The system according to claim 9, wherein at least one of the first opening and the second opening of the sealing member is formed with an angled sidewall.

11. The system according to claim 1, further comprising a medicament carrying tray disposed between the upper layer and the lower layer, the medicament carrying tray being attached to the upper layer and removable from the lower layer.

12. The system according to claim 1, further comprising a medicament carrying tray disposed between the upper layer and a lower layer, the upper layer being attached to the medicament carrying tray.

13. A system for dispensing medicament, the system comprising:
 a housing comprising:
 an airflow channel extending therethrough;
 a portion configured for receiving a medicament container in communication with the airflow channel;
 a lancet disposed in the housing for selectively puncturing or shearing the medicament container in communication with the airflow channel; and
 a sealing member configured for engaging the medicament container when the medicament container is disposed below the lancet, wherein the sealing member comprises a first opening and a second opening spaced apart from the first opening, and
 wherein the first opening and the second opening of the sealing member are each defined, in part, by an angled sidewall, and wherein the angled sidewall of the first opening is set opposite the angled sidewall of the second opening.

14. A system for dispensing medicament, the system comprising:
 a housing comprising:
 an airflow channel extending through the housing;
 a portion of the housing configured for receiving8 a medicament container; and
 a lancet disposed in the housing for selectively puncturing or shearing the medicament container, and a medicament container disposed in the housing, the medicament container having an upper layer and a lower layer forming a receptacle below the upper layer, and a projection extending downwardly from the upper layer and into the receptacle.

15. The system according to claim 14, further comprising a medicament carrying tray disposed between the upper layer and the lower layer, the upper layer being attached to the medicament carrying tray.

16. The system according to claim 14, wherein the medicament container comprises a middle layer disposed between the upper layer and the lower layer, the middle layer forming the projection, and having a first opening and a second opening on opposing sides of the projection.

17. The system according to claim 16, wherein at least one of the first opening and second opening of the middle layer is defined, in part, by an angled sidewall.

18. The system according to claim 17, wherein the first opening and the second opening of the middle layer are formed, in part, with an angled sidewall, and wherein the angled sidewall of the first opening and the angled sidewall of the second opening are disposed opposite one another.

19. The system for dispensing medicament according to claim 14, wherein the lancet has angled ends configured for forcing the punctured or sheared upper layer against the lower layer to minimize interference with medicament entrainment.

20. A system for dispensing medicament according to claim 14, wherein the lancet comprises ends having an outer surface which defines a portion of the airflow channel through the housing when the lancet is not disposed in the medicament container.

21. The system according to claim 14, wherein the airflow channel extends in the first opening in the upper layer and out the second opening in the upper layer of the medicament container.

22. A system for dispensing medicament according to claim 14, further comprising a sealing member configured for engaging the medicament container when the medicament container is disposed below the lancet.

23. The system according to claim 22, wherein the sealing member comprises a first opening and a second opening spaced apart from the first opening.

24. The system according to claim 23, wherein at least one of the first opening and the second opening of the sealing member is formed with an angled sidewall.

25. A system for dispensing medicament, the system comprising:
 a housing comprising:
 a first portion having an airflow channel extending therethrough;
 a second portion configured for receiving a medicament container having an upper layer, a lower layer and medicament disposed therein; and
 a lancet disposed in the housing for selectively puncturing or shearing the upper layer of the medicament container so as to form a first opening and a second opening in the upper layer of the medicament container in alignment with the airflow channel wherein the housing further comprises an airflow control valve disposed along the airflow channel for selectively limiting airflow through the airflow channel.

26. The system according to claim 25, wherein the housing further comprises an initial airflow channel having an airflow vane disposed therein.

27. The system according to claim 26, wherein the airflow vane is disposed in communication with the airflow control valve for selectively opening the airflow control valve.

28. The system according to claim 25, wherein the housing further comprises a deagglomeration channel disposed proximally from the airflow control valve.

29. A system for dispensing medicament, the system comprising:

a housing comprising:

a first portion having an airflow channel extending therethrough;

a second portion configured for receiving a medicament container having an upper layer, a lower layer and medicament disposed therein; and a lancet disposed in the housing for selectively puncturing or shearing the upper layer of the medicament container so as to form a first opening and a second opening in the upper layer of the medicament container in alignment with the airflow channel, and a sealing member configured for engaging the medicament container when the medicament container is disposed below the lancet, wherein the sealing member comprises a first opening and a second opening spaced apart from the first opening, and wherein the first opening and the second opening of the sealing member are each defined, in part, by an angled sidewall, and wherein the angled sidewall of the first opening is set opposite the angled sidewall of the second opening.

30. A system for dispensing medicament, the system comprising:

a housing comprising:

a first portion having an airflow channel extending therethrough;

a second portion configured for receiving a medicament container having an upper layer, a lower layer and medicament disposed therein; and a lancet disposed in the housing for selectively puncturing or shearing the upper layer of the medicament container so as to form a first opening and a second opening in the upper layer of the medicament container in alignment with the airflow channel, the lancet having angled ends configured for forcing the punctured or sheared upper layer against the lower layer to minimize interference with medicament entrainment, and wherein the system further comprises a medicament container disposed in the housing, the medicament container having an upper layer and a lower layer forming a receptacle below the upper layer, and a projection extending downwardly into the receptacle from the upper layer so as to form a flow channel below the projection.

31. The system according to claim 30, wherein the medicament container comprises a middle layer disposed between the upper layer and the lower layer, the middle layer forming the projection, and having a first opening and a second opening on opposing sides of the projection.

32. The system according to claim 31, wherein at least one of the first opening and second opening of the middle layer is defined, in part, by an angled sidewall.

33. The system according to claim 32, wherein the first opening and the second opening of the middle layer are formed, in part, with an angled sidewall, and wherein the angled sidewall of the first opening and the angled sidewall of the second opening are disposed opposite one another.

34. A system for dispensing medicament from a medicament container, the system comprising:

a housing for receiving at least one medicament container and for defining an airflow channel through which medicament flows;

a lancet disposed at least partially within the housing the lancet being configured for forming a first opening and a second opening in a medicament container when the medicament container is disposed in the housing and the lancet is moved from a first position to a second position, wherein the lancet is biased in the first position; and wherein the housing comprises an initial airflow channel independent of the airflow channel associated with the medicament container, and an airflow control valve for selectively regulating airflow through the airflow channel and the initial airflow channel.

35. The system according to claim 34, wherein the lancet comprises a pair of generally solid tapered ends configured for puncturing/shearing an upper wall of a medicament container.

36. The system according to claim 35, wherein the tapered ends of the lancet form a portion of the airflow channel.

* * * * *